US010786218B2

(12) United States Patent
Fukuyo et al.

(10) Patent No.: US 10,786,218 B2
(45) Date of Patent: Sep. 29, 2020

(54) IMAGE DISPLAYING DEVICE, IMAGE PROCESSING DEVICE, RADIOGRAPHIC IMAGING SYSTEM, SECTIONAL IMAGE DISPLAYING METHOD, AND NON-TRANSITORY COMPUTER READABLE MEDIUM

(71) Applicant: FUJIFILM CORPORATION, Minato-ku, Tokyo (JP)

(72) Inventors: Masakazu Fukuyo, Kanagawa (JP); Tomoki Inoue, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 66 days.

(21) Appl. No.: 15/976,007

(22) Filed: May 10, 2018

(65) Prior Publication Data

US 2018/0256126 A1    Sep. 13, 2018

Related U.S. Application Data

(63) Continuation of application No. 14/868,396, filed on Sep. 29, 2015, now Pat. No. 9,993,214.

(30) Foreign Application Priority Data

Sep. 30, 2014    (JP) .................................. 2014-201558

(51) Int. Cl.
*A61B 6/00*    (2006.01)
*A61B 6/02*    (2006.01)
(Continued)

(52) U.S. Cl.
CPC .............. *A61B 6/502* (2013.01); *A61B 6/025* (2013.01); *A61B 6/04* (2013.01); *A61B 6/0407* (2013.01);
(Continued)

(58) Field of Classification Search
CPC ......... A61B 6/025; A61B 6/04; A61B 6/0414; A61B 6/46; A61B 6/461; A61B 6/463;
(Continued)

(56) References Cited

U.S. PATENT DOCUMENTS 5,872,828 A * 2/1999 Niklason ................ A61B 6/025
378/23
6,632,020 B2    10/2003 Kaufhold et al.
(Continued)

FOREIGN PATENT DOCUMENTS

JP    H08-294485 A    11/1996
JP    2010-094397 A    4/2010

OTHER PUBLICATIONS

A translation of JPH08294485 (A) by Patent Translate at EPO on Sep. 24, 2019.*
(Continued)

*Primary Examiner* — Allen C. Ho
(74) *Attorney, Agent, or Firm* — Solaris Intellectual Property Group, PLLC

(57) ABSTRACT

The present invention provides an image displaying device including: a display section that displays a pair of mutually related sectional images; a reception section that, for one of the sectional image pair, receives a successive change instruction for a slice position; a generation section that generates a combined sectional image, corresponding to the slice position of the one sectional image, from the other sectional image of the pair; and a controller that, in cases in which the reception section has received the successive change instruction, effects control to switch display of the one sectional image from the one sectional image being displayed to the one sectional image that corresponds to the slice position indicated in the instruction, and, in conjunction with switching, to successively switch display of the
(Continued)

other sectional image from the other sectional image that is being displayed to the combined sectional image.

11 Claims, 19 Drawing Sheets

(51) Int. Cl.
    *A61B 6/03*            (2006.01)
    *A61B 6/04*            (2006.01)
    *A61B 6/12*            (2006.01)
    *G06T 11/60*          (2006.01)

(52) U.S. Cl.
    CPC .............. *A61B 6/0414* (2013.01); *A61B 6/44* (2013.01); *A61B 6/4429* (2013.01); *A61B 6/4435* (2013.01); *A61B 6/4452* (2013.01); *A61B 6/4458* (2013.01); *A61B 6/46* (2013.01); *A61B 6/461* (2013.01); *A61B 6/463* (2013.01); *A61B 6/467* (2013.01); *A61B 6/488* (2013.01); *A61B 6/52* (2013.01); *G06T 11/60* (2013.01); *A61B 6/12* (2013.01); *A61B 6/5205* (2013.01); *G06T 2210/41* (2013.01)

(58) Field of Classification Search
    CPC ......... A61B 6/467; A61B 6/488; A61B 6/502; A61B 6/52; A61B 6/5205; A61B 6/0407; A61B 6/44; A61B 6/4429; A61B 6/4435; A61B 6/4452; A61B 6/4458
    USPC ....................... 378/22, 25, 26, 37, 62, 98, 21
    See application file for complete search history.

(56) References Cited

U.S. PATENT DOCUMENTS

| | | | |
|---|---|---|---|
| 6,674,835 B2 | 1/2004 | Kaufhold et al. | |
| 6,707,878 B2 | 3/2004 | Claus et al. | |
| 6,751,285 B2 | 6/2004 | Eberhard et al. | |
| 7,218,766 B2 * | 5/2007 | Eberhard | A61B 6/463 128/922 |
| 7,245,698 B2 * | 7/2007 | Pang | A61B 6/025 378/22 |
| 7,453,979 B2 | 11/2008 | Sendai | |
| 7,463,713 B2 * | 12/2008 | Mertelmeier | A61B 6/025 378/22 |
| 7,515,682 B2 * | 4/2009 | Li | A61B 6/025 378/210 |
| 7,577,282 B2 * | 8/2009 | Gkanatsios | A61B 5/0048 382/128 |
| 7,616,801 B2 | 11/2009 | Gkanatsios et al. | |
| 7,630,533 B2 * | 12/2009 | Ruth | G06K 9/4638 382/131 |
| 7,693,254 B2 | 4/2010 | Muller et al. | |
| 7,702,142 B2 * | 4/2010 | Ren | G06T 3/0006 382/131 |
| 7,760,924 B2 * | 7/2010 | Ruth | G06T 11/006 382/128 |
| 7,778,388 B2 * | 8/2010 | Sendai | A61B 6/025 378/22 |
| 7,809,175 B2 | 10/2010 | Roehrig et al. | |
| 7,831,296 B2 * | 11/2010 | DeFreitas | A61B 6/502 600/427 |
| 7,885,440 B2 | 2/2011 | Fram et al. | |
| 7,929,743 B2 * | 4/2011 | Khorasani | A61B 6/025 378/37 |
| 7,992,100 B2 * | 8/2011 | Lundström | G06F 19/321 715/810 |
| 8,044,972 B2 * | 10/2011 | Häll | A61B 6/5235 345/619 |
| 8,051,386 B2 * | 11/2011 | Rosander | G06F 19/321 715/810 |
| 8,175,367 B2 * | 5/2012 | Chan | G06T 7/0012 378/37 |
| 8,184,890 B2 * | 5/2012 | Zhang | A61B 6/502 382/131 |
| 8,192,361 B2 * | 6/2012 | Sendai | A61B 5/0077 378/37 |
| 8,223,916 B2 * | 7/2012 | Srinivas | A61B 6/025 378/21 |
| 8,447,088 B2 * | 5/2013 | Kanagawa | A61B 6/025 378/4 |
| 8,547,402 B2 * | 10/2013 | Kreeger | G16H 50/50 345/634 |
| 8,559,593 B2 * | 10/2013 | Akahori | A61B 6/032 378/115 |
| 8,571,289 B2 | 10/2013 | Ruth et al. | |
| 8,611,492 B2 * | 12/2013 | Jerebko | A61B 6/025 378/22 |
| 8,634,622 B2 * | 1/2014 | Woods | G06K 9/3233 382/131 |
| 8,705,690 B2 * | 4/2014 | Jerebko | A61B 6/025 378/21 |
| 8,798,353 B2 * | 8/2014 | Claus | G06T 11/006 378/37 |
| 8,804,912 B2 * | 8/2014 | Akahori | A61B 6/025 378/163 |
| 8,817,948 B2 | 8/2014 | Kusunoki | |
| 8,903,039 B2 * | 12/2014 | Masumoto | A61B 6/5205 378/21 |
| 8,913,713 B2 * | 12/2014 | Masumoto | A61B 6/502 378/21 |
| 8,942,782 B2 | 1/2015 | Sakaguchi et al. | |
| 8,963,917 B2 | 2/2015 | Yahiro et al. | |
| 9,098,935 B2 | 8/2015 | Endo et al. | |
| 9,113,796 B2 | 8/2015 | Engel et al. | |
| 9,117,315 B2 | 8/2015 | Tajima | |
| 9,129,362 B2 | 9/2015 | Jerebko | |
| 9,146,663 B2 | 9/2015 | Kreeger et al. | |
| 9,256,939 B1 | 2/2016 | Bediz et al. | |
| 9,269,141 B2 * | 2/2016 | Wiemker | G06T 7/0012 |
| 9,289,183 B2 | 3/2016 | Karssemeijer et al. | |
| 9,311,717 B2 | 4/2016 | Serlie et al. | |
| 9,474,497 B2 | 10/2016 | Kopylov | |
| 9,526,471 B2 * | 12/2016 | Goodenough | A61B 6/025 |
| 9,576,380 B2 | 2/2017 | Sugahara et al. | |
| 9,592,019 B2 | 3/2017 | Sugiyama et al. | |
| 9,613,440 B2 * | 4/2017 | Claus | G06T 11/006 |
| 9,629,599 B2 | 4/2017 | Jerebko et al. | |
| 9,659,369 B2 | 5/2017 | Nakayama et al. | |
| 9,675,277 B2 | 6/2017 | Arai et al. | |
| 9,724,047 B2 * | 8/2017 | Hörnig | G06T 11/006 |
| 9,730,669 B2 | 8/2017 | Lee et al. | |
| 9,799,109 B2 | 10/2017 | Lee et al. | |
| 9,805,507 B2 | 10/2017 | Chen et al. | |
| 9,808,213 B2 | 11/2017 | Endo et al. | |
| 9,855,013 B2 | 1/2018 | Morita et al. | |
| 9,861,332 B2 * | 1/2018 | Fukuda | A61B 6/5205 |
| 9,949,706 B2 * | 4/2018 | Fukuda | A61B 6/025 |
| 9,993,214 B2 * | 6/2018 | Fukuyo | G06T 11/60 |
| 10,043,294 B2 * | 8/2018 | Fukuda | A61B 6/025 |
| 10,070,839 B2 * | 9/2018 | Westerhoff | G06T 15/08 |
| 10,111,631 B2 * | 10/2018 | Gkanatsios | A61B 6/025 |
| 10,271,801 B2 * | 4/2019 | Nakayama | A61B 6/502 |
| 10,278,660 B2 * | 5/2019 | Fukuda | A61B 6/461 |
| 10,335,103 B2 * | 7/2019 | Sugahara | A61B 6/0492 |
| 10,335,107 B2 * | 7/2019 | Fukuda | A61B 6/4452 |
| 10,433,795 B2 * | 10/2019 | Nakayama | A61B 6/5205 |
| 10,624,598 B2 * | 4/2020 | Chen | A61B 6/463 |

OTHER PUBLICATIONS

English language translation of the following: Office action dated Dec. 6, 2017 from the JPO in a Japanese patent application No. 2014-201558 corresponding to the instant patent application.
Office action dated Jun. 29, 2017 from the US Patent Office in U.S. Appl. No. 14/868,396.
Notice of Allowance dated Feb. 13, 2018 from the US Patent Office in U.S. Appl. No. 14/868,396.

(56) References Cited

OTHER PUBLICATIONS

Office Action dated Jul. 2, 2019, issued by the SIPO in corresponding Chinese Patent Application No. 201510633589.3.
Office Action dated Jan. 7, 2020, issued by the SIPO in corresponding Chinese Patent Application No. 201510633589.3.

* cited by examiner

FIG.9
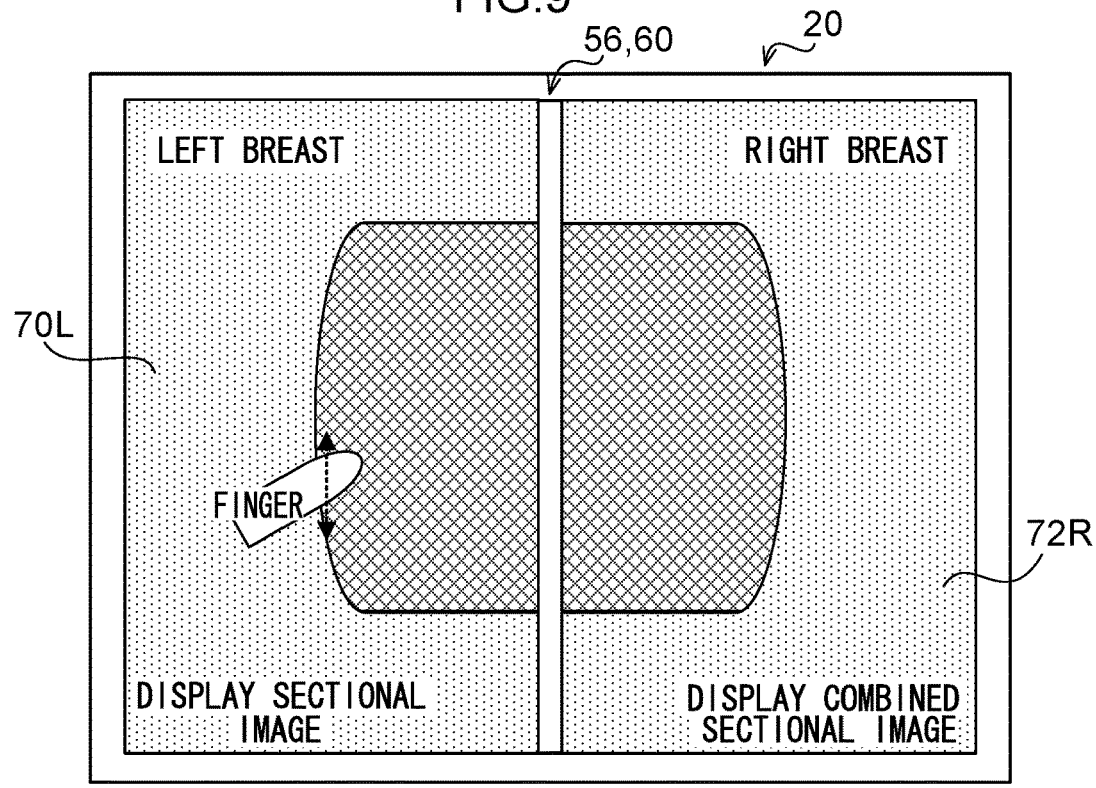
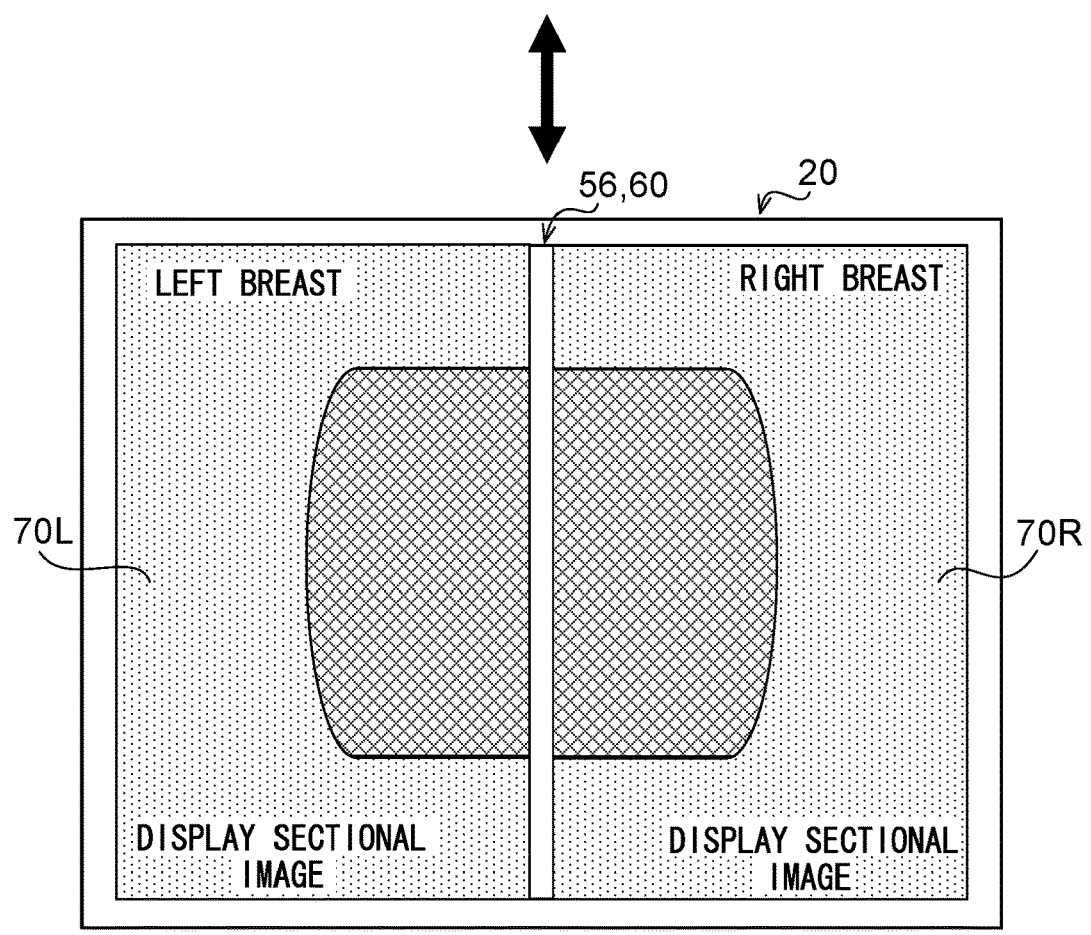

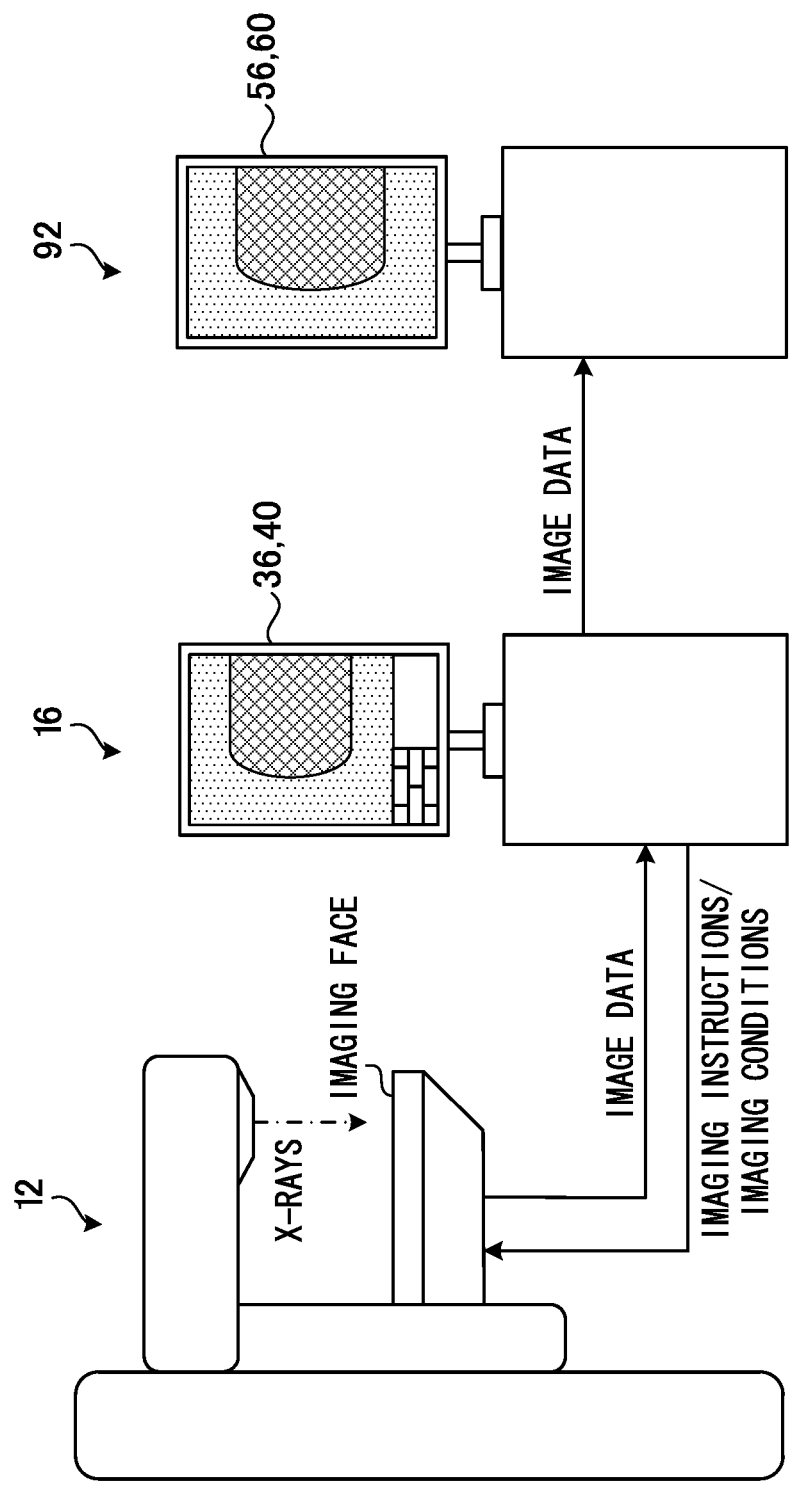

IMAGE DISPLAYING DEVICE, IMAGE PROCESSING DEVICE, RADIOGRAPHIC IMAGING SYSTEM, SECTIONAL IMAGE DISPLAYING METHOD, AND NON-TRANSITORY COMPUTER READABLE MEDIUM

CROSS-REFERENCE TO RELATED APPLICATIONS

The present application is a continuation of U.S. application Ser. No. 14/868,396, filed Sep. 29, 2015, issued as U.S. Pat. No. 9,993,214 on Jun. 12, 2018, which claims priority under 35 U.S.C. § 119 from Japanese Patent Application No. 2014-201558, filed on Sep. 30, 2014. Each of the applications listed above is incorporated by reference, in its entirety, into the present application.

BACKGROUND OF THE INVENTION

Field of the Invention

The present invention relates to an image displaying device, an image processing device, a radiographic imaging system, a sectional image displaying method, and a non-transitory computer readable medium storing a sectional image displaying program.

Description of the Related Art

For medical diagnostic purposes, radiation is irradiated onto an imaging target of an examinee, who is a patient, and radiographic images are imaged using a radiographic imaging device. There are known examples of such radiographic imaging devices that image radiographic images of the breasts of an examinee, in what is referred to as mammography.

As such imaging methods, tomosynthesis imaging is known in which radiation is irradiated onto a breast from plural directions so as to image radiographic images, and a sectional image is generated based on the imaged radiographic images.

In tomosynthesis imaging, since plural sectional images are generally generated, there is technology to display to a user, such as a doctor who is reading a sectional image for diagnosis or the like, which position (slice) the sectional image being read corresponds to.

SUMMARY OF THE INVENTION

The present invention provides an image displaying device, an image processing device, a radiographic imaging system, a sectional image displaying method, and a non-transitory computer readable medium storing a sectional image displaying program that are, in cases in which a pair of related sectional images are displayed, coupled to switching slice position of one sectional image, capable of smoothly switching display of the other sectional image.

A first aspect of the present invention is an image displaying device, including: a display section that displays a pair of mutually related sectional images; a reception section that, for one sectional image of the pair of sectional images being displayed at the display section, receives a successive change instruction for a slice position; a generation section that generates a combined sectional image, corresponding to the slice position of the one sectional image, from the other sectional image of the pair of sectional images; and a controller that, in cases in which the reception section has received the successive change instruction, effects control so as to switch display of the one sectional image from the one sectional image being displayed to the one sectional image that corresponds to the slice position indicated in the successive change instruction, and, in conjunction with the switching, so as to successively switch display of the other sectional image from the other sectional image that is being displayed to the combined sectional image.

In a second aspect of the present invention, in the above aspect, the generation section, by combining two frames of the other sectional image that are close to a slice position corresponding to the combined sectional image at a combination proportion, may generate the combination proportion according to a slice position corresponding to the combined sectional image and slice positions corresponding to the two frames of the other sectional image.

In a third aspect of the present invention, in the above aspects, in cases in which the reception section has received the successive change instruction, the generation section may generate a combined sectional image, corresponding to the slice position of the one sectional image, from the other sectional image of the pair of sectional images; and the controller may effect control so as to switch display of the one sectional image from the one sectional image begin displayed to the one sectional image that corresponds to the slice position indicated in the successive change instruction, and, in conjunction with the switching, so as to successively switch display of the other sectional image from the other sectional image being displayed to the combined sectional image.

In a fourth aspect of the present invention, in the above aspects, after the reception section has finished receiving the successive change instruction, the controller may switch display of the other sectional image from the combined sectional image being displayed to the other sectional image corresponding to a slice position that is closest to a slice position corresponding to the combined sectional image.

In a fifth aspect of the present invention, in the above aspects, in cases in which the slice position indicated in the successive change instruction is a slice position having the largest value in the one sectional image, the controller may employ the other sectional image corresponding to the largest value of the other slice positions for display of the other sectional image; and in cases in which the slice position indicated in the successive change instruction is a slice position having the smallest value in the one sectional image, the controller may employ the other sectional image corresponding to the smallest value of the other slice positions for display of the other sectional image.

In a sixth aspect of the present invention, in the above aspects, the generation section may further generate a combined sectional image corresponding to a slice position between a predetermined plural slice positions corresponding to the one sectional image.

In a seventh aspect of the present invention, in the above aspects, after the reception section has received a successive change instruction for a slice position from a first slice position to a second slice position, in cases in which the reception section further receives a successive change instruction for a third slice position during a period in which successive switching of the combined sectional image is being performed by the controller according to the successive change instruction, the controller may effect control to stop the successive switching of display of the other sectional image and, after displaying the other sectional image at a slice position close to the second slice position in a successive switching direction, to successively switch from the sectional image being displayed to the combined sectional image corresponding to the third slice position.

In an eighth aspect of the present invention, in the first to sixth aspects, after the reception section has received a successive change instruction for a slice position from a first slice position to a second slice position, in cases in which the reception section further receives a successive change instruction for a third slice position during a period during a period in which successive switching of the combined sectional image is being performed by the controller according to the successive change instruction, for display of the other sectional image, the generation section may generate a new combined sectional image combined from the combined sectional image being displayed and the other sectional image, at a combination proportion according to a slice position corresponding to the combined sectional image being displayed and the third slice position, and the controller may effect control to stop the successive switching of display of the other sectional image and to successively switch to the new combined sectional image.

A ninth aspect is an image displaying device, including: a display section that displays a pair of mutually related sectional images; a reception section that, for one sectional image of the pair of sectional images being displayed at the display section, receives a successive change instruction for a slice position; a generation section that generates a combined sectional image, corresponding to a slice position between slice positions of the one sectional image, from the other sectional image of the pair of sectional images; and a controller that, in cases in which the reception section has received the successive change instruction, effects control so as to switch display of the one sectional image from the one sectional image being displayed to the one sectional image that corresponds to the slice position indicated in the successive change instruction, and, in conjunction with the switching, so as to successively switch display of the other sectional image from the other sectional image that is being displayed to the combined sectional image or to a sectional image.

A tenth aspect of the present invention is an image processing device, including: a reception section that receives a successive change instruction for a slice position for one sectional image of a pair of mutually related sectional images being displayed at a display section that displays the pair of sectional images; a generation section that generates a combined sectional image, corresponding to the slice position of the one sectional image, from the other sectional image of the pair of sectional images; and a controller that, in cases in which the reception section has received the successive change instruction, effects control so as to switch display of the one sectional image from the one sectional image being displayed to the one sectional image that corresponds to the slice position indicated in the successive change instruction, and, in conjunction with the switching, so as to successively switch display of the other sectional image from the other sectional image that is being displayed to the combined sectional image.

An eleventh aspect of the present invention is a radiographic imaging system, including: a radiographic imaging device that images a radiographic image of an imaging target; and the image displaying device of the first aspect, which displays a sectional image generated based on the radiographic image imaged by the radiographic imaging device.

A twelfth aspect of the present invention is a radiographic imaging system, including: a radiographic imaging device that images a radiographic image of an imaging target; a display section that displays a sectional image generated based on the radiographic image imaged by the radiographic imaging device; and the image processing device of the tenth aspect, which performs image processing of the sectional image for display at the display section.

A thirteenth aspect of the present invention is a sectional image displaying method, including: by a reception section, receiving a successive change instruction for a slice position for one sectional image of a pair of mutually related sectional images being displayed at a display section that displays the pair of sectional images; by a generation section, generating a combined sectional image, corresponding to the slice position of the one sectional image, from the other sectional image of the pair of sectional images; and in cases in which the successive change instruction has been received by the reception section, by a controller, effecting control so as to switch display of the one sectional image from the one sectional image being displayed to the one sectional image that corresponds to the slice position indicated in the successive change instruction, and, in conjunction with the switching, so as to successively switch display of the other sectional image from the other sectional image that is being displayed to the combined sectional image.

A fourteenth aspect of the present invention is a non-transitory computer readable medium storing a sectional image display program that causes execution of processing, the processing including: receiving a successive change instruction for a slice position for one sectional image of a pair of mutually related sectional images being displayed at a display section that displays the pair of sectional images; generating a combined sectional image, corresponding to the slice position of the one sectional image, from the other sectional image of the pair of sectional images; and in cases in which the successive change instruction has been received, effecting control so as to switch display of the one sectional image from the one sectional image being displayed to the one sectional image that corresponds to the slice position indicated in the successive change instruction, and, in conjunction with the switching, so as to successively switch display of the other sectional image from the other sectional image that is being displayed to the combined sectional image.

As explained above, the above aspects of the present invention are capable of providing an image displaying device, an image processing device, a radiographic imaging system, a sectional image displaying method, and a non-transitory computer readable medium storing a sectional image displaying program, that are, in cases in which a pair of related sectional images are displayed, coupled to switching slice position of the one sectional image, capable of smoothly switching display of the other sectional image.

BRIEF DESCRIPTION OF THE DRAWINGS

Exemplary embodiments of the present invention will be described in detail based on the following figures, wherein:

FIG. 9 is an explanatory diagram to explain a specific example in which a left breast is displayed by a sectional image, and a right breast is displayed by switching between a combined sectional image and a sectional image, on a display section of a portable data terminal device;

FIG. 19 is a schematic configuration diagram illustrating an outline overall configuration of a radiographic imaging system in a case in which a device equivalent to a personal computer is provided instead of a portable data terminal device.

DETAILED DESCRIPTION OF THE INVENTION

First Exemplary Embodiment

Detailed explanation follows regarding exemplary embodiments of the present invention, with reference to the drawings. Note that the exemplary embodiments do not limit the invention.

Figure 1:
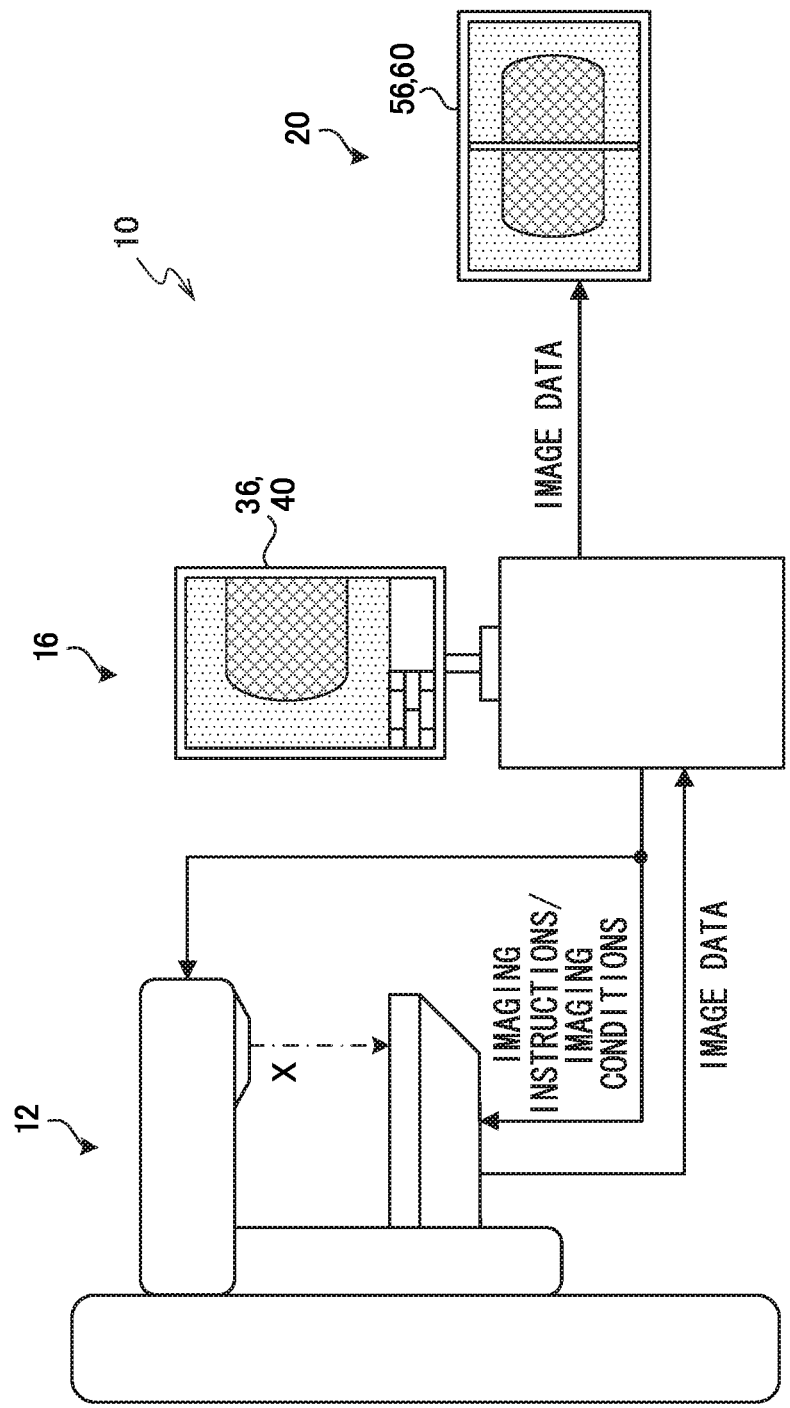
FIG. 1 is a schematic configuration diagram illustrating a schematic overall configuration of a radiographic imaging system of a first exemplary embodiment.
Figure 2:
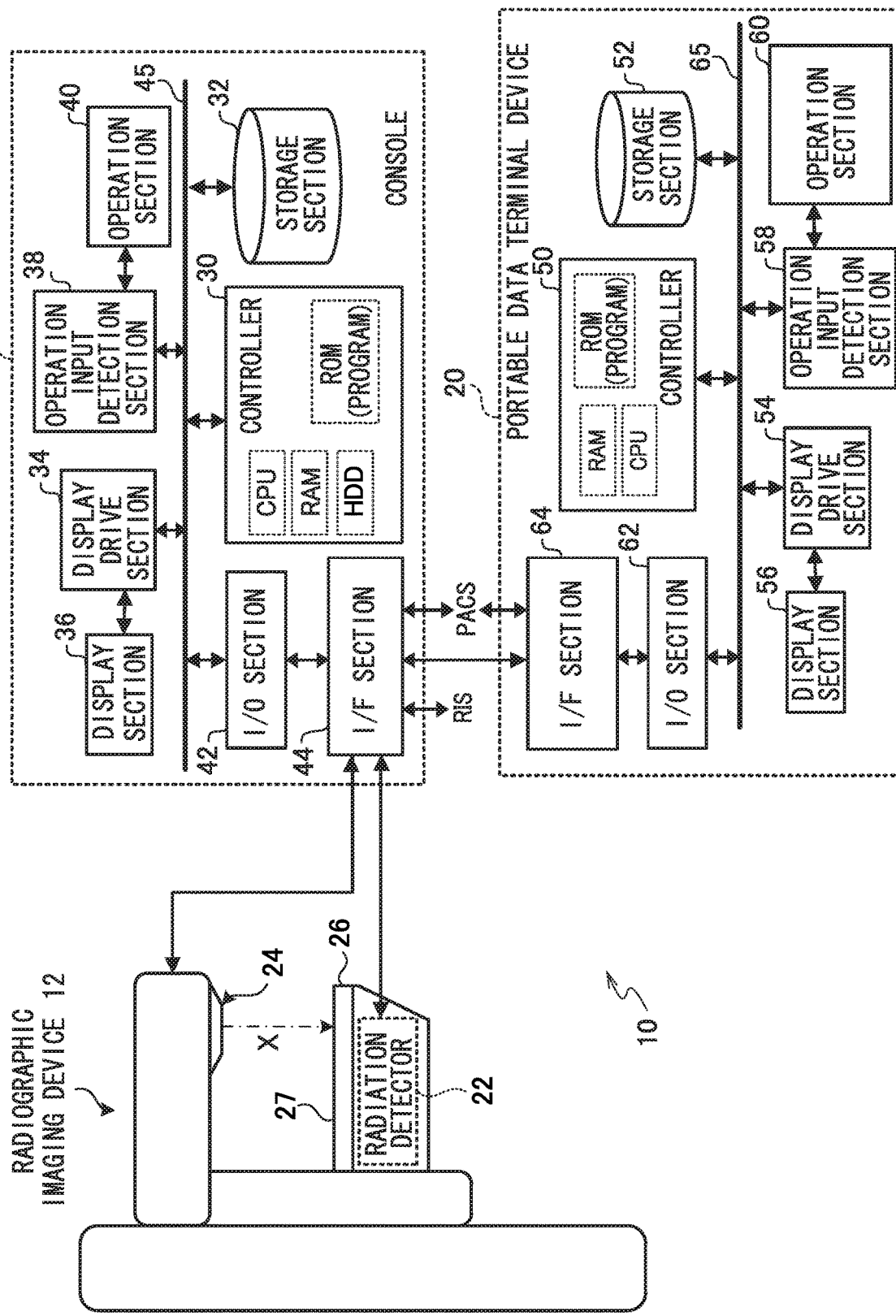
FIG. 2 is a functional block diagram illustrating a schematic configuration to explain the function of a console and a portable data terminal device in a radiographic imaging system of the first exemplary embodiment.

Explanation first follows regarding a schematic configuration of an overall radiographic imaging system 10 of the present exemplary embodiment. FIG. 1 illustrates a schematic configuration of an overall configuration of the radiographic imaging system 10 of the present exemplary embodiment. FIG. 2 is a functional block diagram illustrating a schematic configuration to explain the function of a console 16 and a portable data terminal device 20 in the radiographic imaging system 10 of the present exemplary embodiment.

A radiographic imaging system 10 of the present exemplary embodiment includes a function to image radiographic images based on instructions (an imaging menu) input from an external system (for example a Radiology Information System (RIS)) through the console 16 by operation of a user, such as a doctor or radiographer.

The radiographic imaging system 10 of the present exemplary embodiment includes a radiographic imaging device 12, the console 16, and the portable data terminal device 20.

Explanation follows regarding of a case in the radiographic imaging system 10 of the present exemplary embodiment in which the console 16 generates sectional images based on radiographic images imaged by tomosynthesis imaging by the radiographic imaging device 12, and the generated sectional images are, for example, viewed and read by a user using the portable data terminal device 20.

The radiographic imaging device 12 of the present exemplary embodiment is a device that images radiographic images of the breasts of examinees in, for example, what is referred to as, mammography. The radiographic imaging device 12 may be a device that images the breast of the examinee with the examinee in a seated state, such as sat on a chair (including a wheelchair), and is a device at least capable of imaging the left and right breasts of an examinee separately with the upper body of the examinee in an upright state.

The radiographic imaging device 12 includes a radiation source 24, such as an x-ray tube, that is provided facing toward an imaging face 27 of an imaging table 26, and irradiates X-rays from the radiation source 24 toward the imaging face 27.

To image a radiographic image of the breast of the examinee, the breast on one side, this being the imaging target, is immobilized by being compressed between a press plate (see FIG. 3) and the imaging face 27 of the imaging table 26, and X-rays are irradiated from the radiation source 24 onto the immobilized breast.

Figure 3:
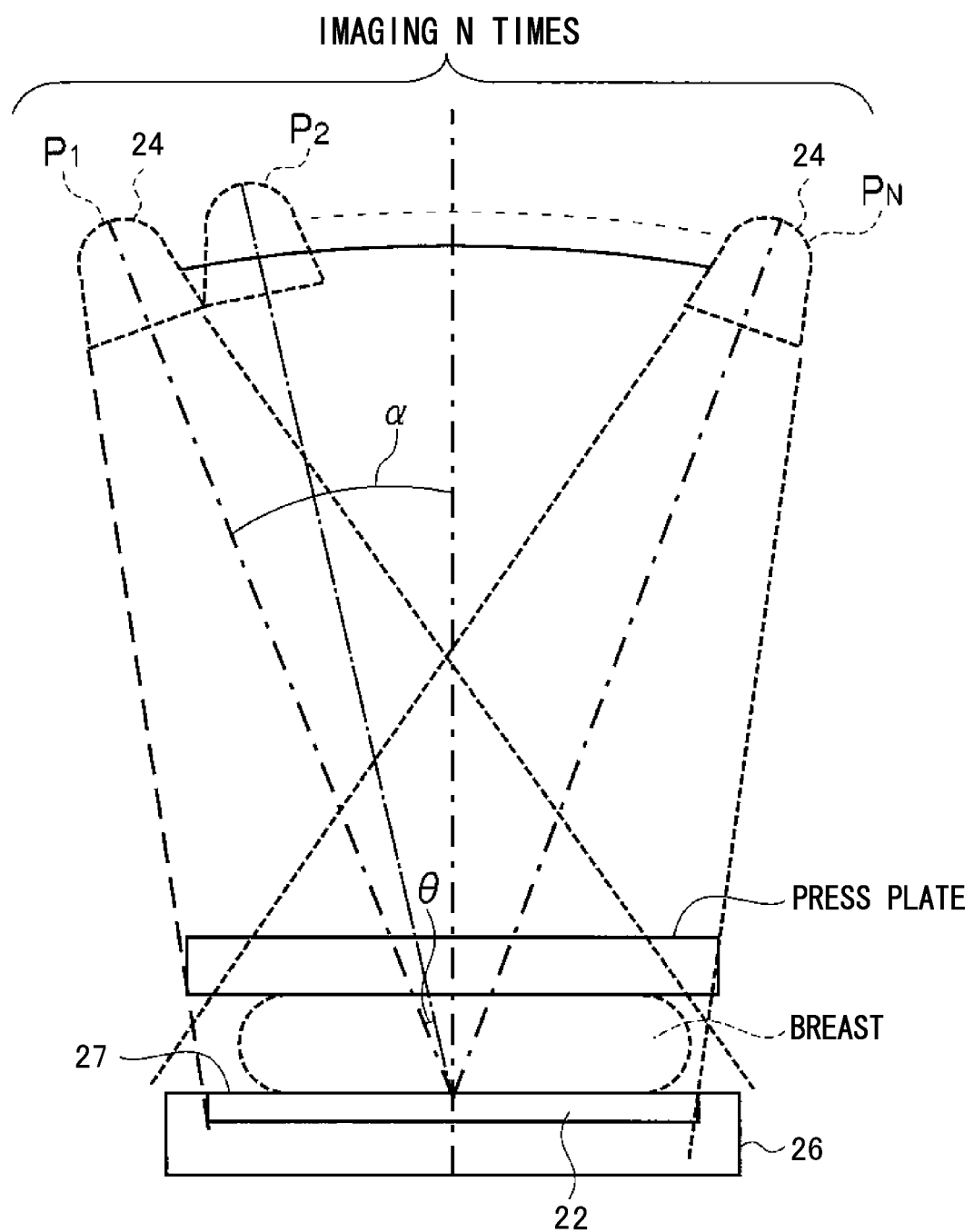
FIG. 3 is an explanatory diagram to explain tomosynthesis imaging in a radiographic imaging device of the first exemplary embodiment.

The radiographic imaging device 12 of the present exemplary embodiment is device capable of at least performing imaging of a breast as the imaging target from plural directions, in which is referred to as tomosynthesis imaging. FIG. 3 is an explanatory diagram to explain tomosynthesis imaging in the radiographic imaging device 12 of the present exemplary embodiment. In the radiographic imaging device 12, as illustrated in FIG. 3, in a case in which imaging is performed of a breast from plural directions (tomosynthesis imaging), the radiation source 24 moves in a circular arc shape. In the present exemplary embodiment, the imaging position is moved from an angle $\alpha$ by steps of a specific angle $\theta$, as illustrated in FIG. 3, and imaging is performed with the position of the radiation source 24 at N locations, P1 to PN.

A radiation detector 22, installed inside the imaging table 26, is irradiated with X-rays that have passed through the breast that is the imaging target and through the imaging face 27, and detects the X-rays. The X-rays detected by the radiation detector 22 are visualized by generating a radiographic image. The radiation detector 22 is irradiated by the X-rays carrying the image data, records image data expressing a radiographic image, and outputs the recorded image data. Charges are generated for each pixel according to the dose of X-rays irradiated, and detected as image data. The radiation detector 22 according to the present exemplary embodiment is an electronic cassette, and is, for example, a digital radiography (DR) cassette provided with a radiosensitive layer that converts the radiation into digital data, and outputs the digital data.

In the present exemplary embodiment, the image data expressing the radiographic images output from the radiation detector 22 of the radiographic imaging device 12 is transmitted to the console 16. The console 16 according to the present exemplary embodiment controls the radiographic imaging device 12 by using an imaging menu, various data, and the like acquired from external systems and the like through a wireless Local Area Network (LAN) or the like. The console 16 of the present exemplary embodiment performs transmission and reception of various data with the radiation detector 22 of the radiographic imaging device 12. The console 16 of the present exemplary embodiment generates a sectional image based on the radiographic images acquired from the radiation detector 22, and transmits the generated sectional image to the portable data terminal device 20.

The console 16 of the present exemplary embodiment is a server/computer that serves as an example of an image processing device. As illustrated in FIG. 2, the console 16 includes a controller 30, a storage section 32, a display drive section 34, a display section 36, an operation input detection section 38, an operation section 40, an input/output (I/O) section 42, and an interface (I/F) section 44. The controller 30, the storage section 32, the display drive section 34, the operation input detection section 38, and the I/O section 42 are connected together so as to enable exchange of data and the like with each other through a bus 45, such as a system bus or a control bus.

The controller 30 i controls the overall operation of the console 16. The controller 30 generates a sectional image based on radiographic images obtained by tomosynthesis imaging. The controller 30 of the present exemplary embodiment includes a Central Processing Unit (CPU), Read Only Memory (ROM), Random Access Memory (RAM), and a Hard Disk Drive (HDD). The CPU has functionality to control the overall operation of the console 16. Various programs and the like for use by the CPU are pre-stored in the ROM. The RAM temporarily stores various data. The HDD stores and retains various data. The HDD may be a Solid State Drive (SSD), and may be commonly employed as the storage section 32.

The display drive section 34 controls display of various data on the display section 36. The display section 36 of the present exemplary embodiment displays an imaging menu, radiographic images, sectional images, etc. The operation input detection section 38 detects the operation status and processing operations of the operation section 40. The operation section 40 is employed for a user to perform instructions related to imaging radiographic images, generating sectional images, etc. The operation section 40 may, for example, be embodied by a keyboard and mouse, and may be integrated together with the display section 36 and embodied by a touch panel. The operation section 40 may include a camera, and be embodied such that various instructions are input by the camera recognizing gestures of the user.

The I/O section 42 and the I/F section 44 performs wired or wireless communication for transmission and reception of various data with the radiographic imaging device 12 (the radiation source 24, the radiation detector 22, etc.), the portable data terminal device 20, an external system such as a RIS, and an external system such as a picture archiving and communication system (PACS).

The storage section 32 stores various data, such as image data of the radiographic images, and image data of the sectional images (described in detail below).

The portable data terminal device 20, which is an example of an image displaying device, receives sectional images from the console 16, and to present (display) to the user the received radiographic images, and sectional images (described in detail below) generated based on the radiographic images. The portable data terminal device 20 of the present exemplary embodiment is what is referred to as a Personal Digital Assistant (PDA) that is capable of being driven by an internal battery, with specific examples thereof including a tablet terminal and a smartphone.

As illustrated in FIG. 2, the portable data terminal device 20 according to the present exemplary embodiment includes a controller 50, a storage section 52, a display drive section 54, a display section 56, an operation input detection section 58, an operation section 60, an I/O section 62, and an I/F section 64. The controller 50, the storage section 52, the display drive section 54, the operation input detection section 58, and the I/O section 62 are connected together so as to be capable of exchanging data etc. through a bus 65, such as a system bus or a control bus.

The controller 50 is an example of a generation section and a controller, and includes functionality to control the overall operation of the portable data terminal device 20. The controller 50 includes a CPU, ROM, and RAM. The CPU controls the overall operation of the portable data terminal device 20. Various processing programs and the like for use by the CPU are pre-stored in the ROM. The RAM temporarily stores various data.

The display drive section 54 controls display of various data, including various types of image data, on the display section 56. The operation input detection section 58 detects the operation status and processing operations of the operation section 60. In the present exemplary embodiment, the operation section 60 is employed for a user to perform instructions such as to instruct the slice position of a sectional image to display on the display section 56. In the present exemplary embodiment, the operation section 60 may include, for example, a touch panel, a touch pen, plural keys, or a mouse. In cases in which the operation section 60 is embodied by a touch panel then it may also serve as the display section 56.

The I/O section 62 and the I/F section 64 are an example of a reception section, and performs wireless communication, optical communication using light, or the like, for the transmission of various data to and from the console 16 and a PACS.

The storage section 52 stores sectional images acquired from the console 16. More specifically, the storage section 52 stores sectional images generated by the console 16 and corresponding to plural respective slice positions. Specific examples of the storage section 52 include non-volatile memory.

In the present exemplary embodiment, various programs stored in the controller 30 of the console 16 and in the controller 50 of the portable data terminal device 20 are pre-stored in ROM of the controller 30 and the controller 50, however there is no limitation thereto, and configuration may be made such that programs are stored on a recording medium such as a Compact Disk Read Only Memory (CD-ROM) or removable disk, and then installed from the recording medium onto ROM or the like. Configuration may be made such that the programs are installed on ROM or the like from an external device, via a communication line such as the internet.

Explanation follows regarding operation of the radiographic imaging system 10 of the present exemplary embodiment, with reference to the drawings.

Explanation first follows regarding imaging radiographic images in the radiographic imaging device 12 of the present exemplary embodiment. In such case, imaging radiographic images is executed in the radiographic imaging device 12 according to an imaging menu.

The examinee places the breast on one side that is the imaging target in contact with the imaging face 27 of the radiographic imaging device 12. The radiographic imaging device 12 moves a press plate (see FIG. 3) toward the imaging face 27, and immobilizes the breast.

In the radiographic imaging device 12 according to the present exemplary embodiment, from this state, in cases in which an instruction has been input to perform tomosynthesis imaging by imaging the breast from plural directions, the radiation source 24 is moved in a circular arc shape without moving the imaging table 26. The imaging position is moved from an angle $\alpha$ by steps of a specific angle $\theta$, as illustrated in FIG. 3, and X-rays are irradiated based on each of the imaging conditions with the position of the radiation source 24 at N locations, P1 to PN. X-rays, separately irradiated from the radiation source 24, reach the radiation detector 22 after passing through the respective breasts.

On irradiation with X-rays, the radiation detector 22 outputs image data representing the respective irradiated radiographic images to the console 16. Image data for N frames of radiographic images are output to the console 16 in cases in which, as described above, X-rays are irradiated with the radiation source 24 positioned in N locations, P1 to PN.

Thus, in a case in which plural radiographic images are imaged by tomosynthesis imaging in the radiographic imaging device 12, the console 16 acquires image data of the plural imaged radiographic images, and generates a sectional image of the breast of the examinee.

The controller 30 of the console 16, as described above, reconstructs a sectional image from plural radiographic images obtained by tomosynthesis imaging, and generates a sectional image parallel to the imaging face 27. In the present exemplary embodiment, "parallel" includes substantially parallel. The position in the depth direction of the section in the present exemplary embodiment is referred to as the slice position. The slice position is defined with reference to the imaging face 27, with the slice position of the imaging face 27 set as "0", and with the slice position becoming shallower (higher) (see FIG. 5) on approaching the radiation source 24 (on progression upward in FIG. 1 and FIG. 2).

The controller 30 generates sectional images from plural radiographic images imaged at positions P1, P2, P3, and so on to PN, illustrated in FIG. 3. Thus, in the console 16 of the present exemplary embodiment, the radiographic images received from the radiation detector 22 and obtained by tomosynthesis imaging are stored in the storage section 32. The radiographic images obtained by tomosynthesis imaging may be deleted after the sectional images have been generated; however, they are preferably left stored in preparation for cases in which, for example, a further sectional image is generated with a slice position different to the generated sectional images.

The imaging position of the object of interest on the radiographic images differs according to the imaging angle at which X-rays are irradiated from each of the positions of the radiation source 24. In the controller 30, the moved amount is calculated for the object of interest between the plural radiographic images based on the imaging angle at which the radiographic images were imaged, and a sectional image is reconstructed corresponding to the desired slice position according to a known reconstruction method. The imaging angle maybe acquired from the radiographic imaging device 12 (the radiation detector 22), and may be acquired from an imaging menu or the like. The slice position (or the slice interval) may be acquired by a user instructing the slice position (or slice interval) using the operation section 40 or the like, or may be acquired from an imaging menu or the like.

The sectional image generated by the console 16 may be displayed on the display section 36.

The sectional image generated in the console 16 is associated with the slice position and transmitted to the portable data terminal device 20.

The controller 50 of the portable data terminal device 20 displays sectional images received through the I/F section 64 and the I/O section 62 on the display section 56. In the portable data terminal device 20 of the present exemplary embodiment, the sectional images received from the console 16 are stored in the storage section 52.

Figure 4:
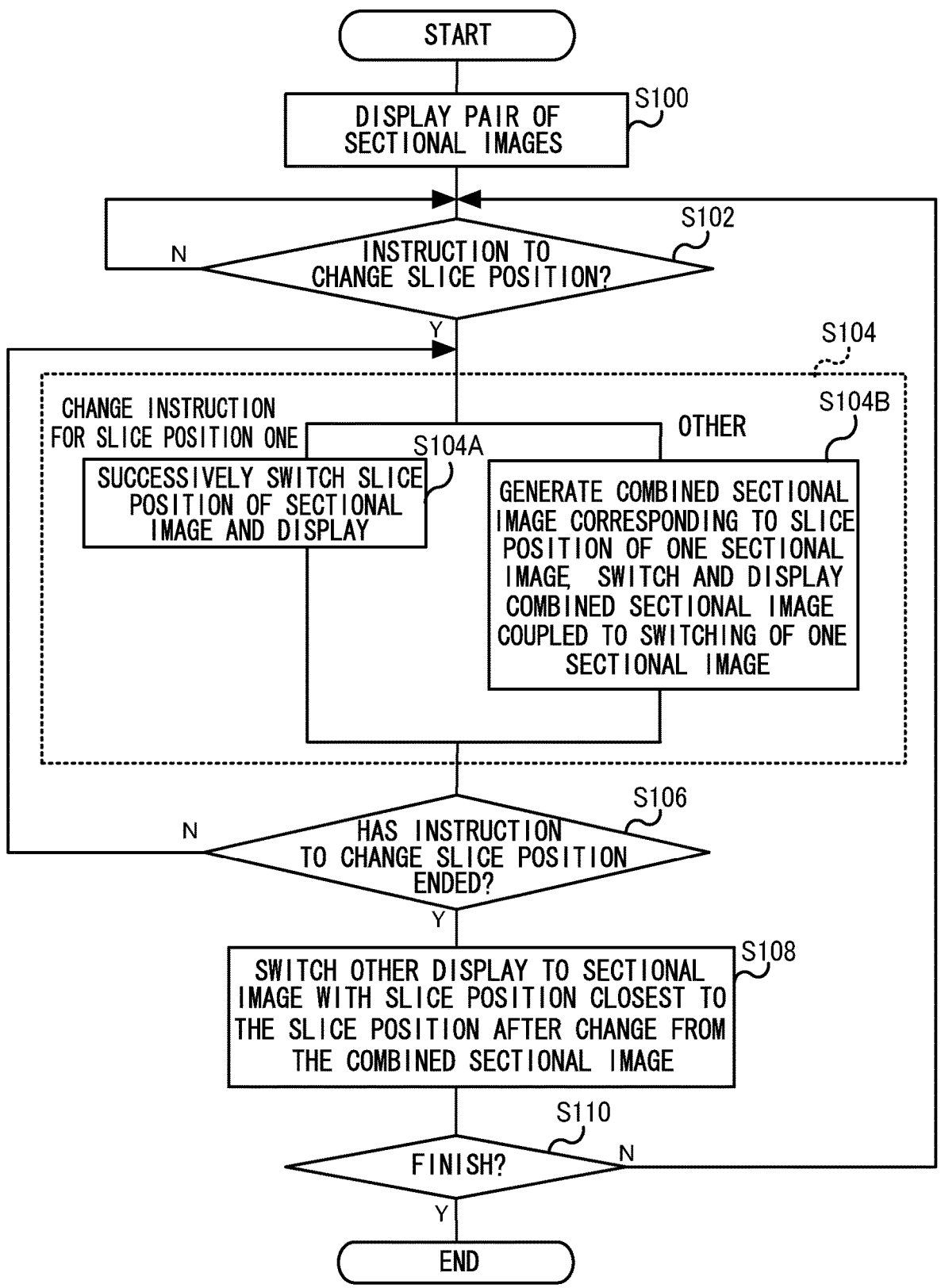
FIG. 4 is a flowchart of sectional image display processing executed by a controller of a portable data terminal device of a first exemplary embodiment.

Explanation follows regarding sectional image display processing executed by the controller 50 of the portable data terminal device 20 of the present exemplary embodiment. FIG. 4 illustrates a flowchart of one example of sectional image display processing executed in the controller 50 of the portable data terminal device 20 of the present exemplary embodiment. Explanation follows regarding a case in the present exemplary embodiment of a specific example in which the portable data terminal device 20 is a tablet terminal including a touch panel in which the display section 56 and the operation section 60 have been integrated together.

Figure 5:
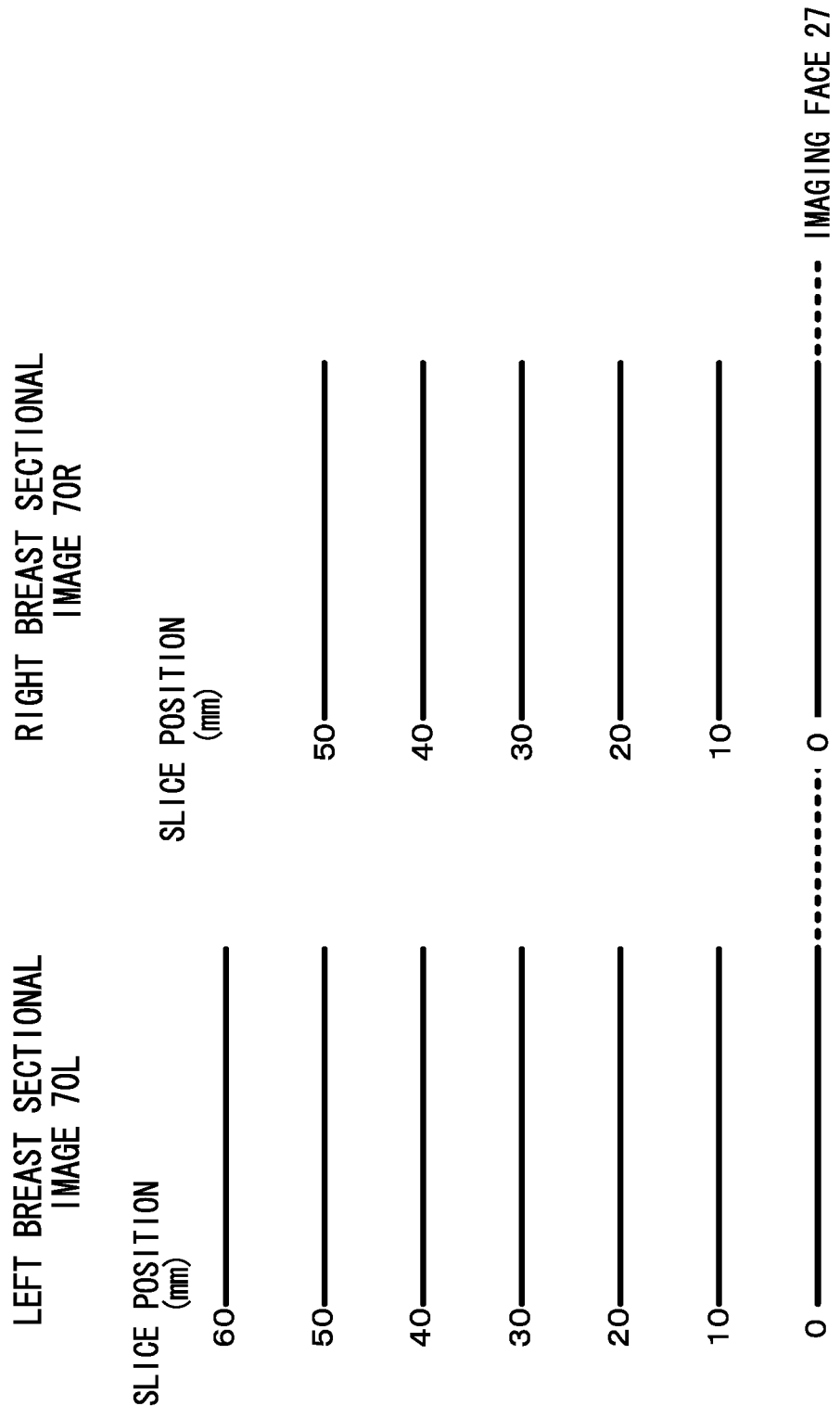
FIG. 5 is an explanatory diagram to explain sectional image of a right breast.

At step S100, the controller 50 of the portable data terminal device 20 displays a pair of mutually related sectional images on the display section 56. Explanation follows regarding a case that employs, as a specific example of pairs of mutually related sectional images, sectional images corresponding to respective plural slice positions of the right breast, and sectional images corresponding to respective plural slice positions of the left breast of the examinee. FIG. 5 is an explanatory diagram to explain a specific example of the sectional images of the left and right breasts. In the specific example illustrated in FIG. 5, left breast sectional images 70L include 7 frames of the left breast sectional images 70L taken with a slice position of the imaging face 27 as 0, at slice thicknesses of 10 mm up to a slice position of 60 mm. The right breast sectional images 70R include 6 frames of the right breast sectional images 70R taken with a slice position of the imaging face 27 as 0, at slice thicknesses of 10 mm up to a slice position of 50 mm. Thus in the specific example of the present exemplary embodiment, there are less frames of sectional images 70 for the right breast sectional images 70R than for the left breast sectional image 70L. There are cases in which the number of frames of the left and right breast sectional images 70 (pairs of the sectional images 70) differ from each other due to, for example, the sizes of the breasts, the manner in which pressing was performed, or due to employing different slice thicknesses on the left and right.

Figure 6:
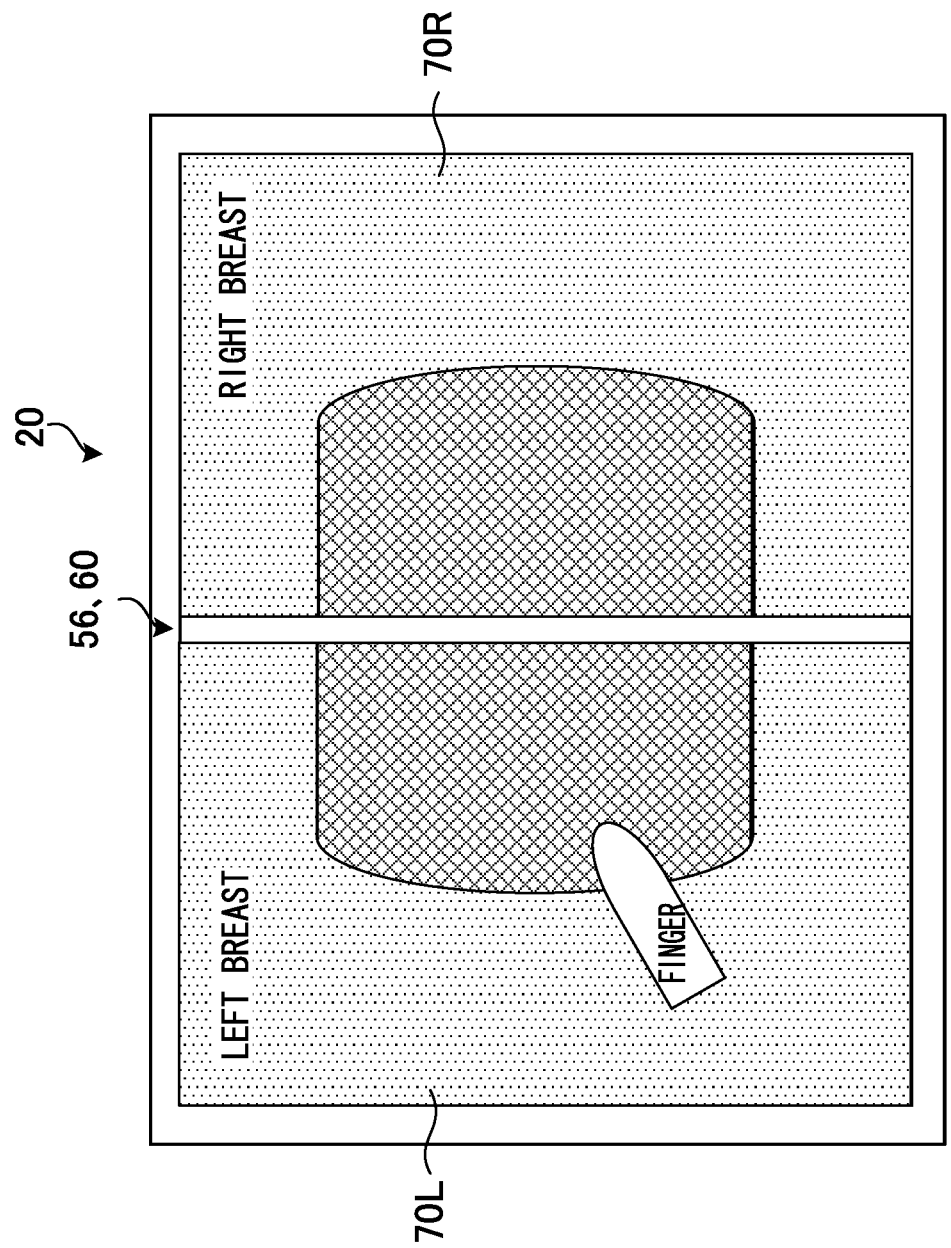
FIG. 6 is a diagram illustrating a specific state in which a sectional image of a left breast, and a sectional image of a right breast, are displayed on a display section of a mobile data terminal device.

In the present exemplary embodiment, explanation follows regarding of a case in which the right breast sectional image and the left breast sectional image are to be displayed on the display section 56 of the portable data terminal device 20. FIG. 6 illustrates a specific example of a state in which the left breast sectional image 70L and the right breast sectional image 70R are displayed on the display section 56 of the portable data terminal device 20. FIG. 6 illustrates a specific example in which a user touches the left breast sectional image 70L displayed on the display section 56 with a finger. In the following, left breast sectional images of the examinee are referred to as "sectional images 70L" irrespective of the slice position, and similarly right breast sectional images of the examinee are referred to as "sectional images 70R". In cases in which discrimination is not made between the sectional images of the left and right breasts, sectional images are referred to collectively as "sectional images 70".

In the processing of step S100, as a specific example in the portable data terminal device 20 of the present exemplary embodiment, the slice positions of the sectional images 70 displayed on the display section 56 are slice positions "0 mm" where the slice positions have the smallest values of slice position for both the sectional images, namely the left and right breast sectional images 70 having slice positions corresponding to the imaging face 27 are displayed on the display section 56, however they are not particularly limited. The slice position of the sectional images 70 displayed is preferably the same in the left and right breasts, or corresponding positions (described in detail below). For example, the sectional image 70L with slice position of "60 mm" for the left breast and the sectional image 70R of the slice position "50 mm" for the right breast may be displayed on the display section 56 such that both slice positions are at maximum values.

In the next step S102, determination is made as to whether or not the controller 50 of the portable data terminal device 20 has instructed the slice position of the sectional images 70 to be changed successively.

In the present exemplary embodiment, in a case in which a user desires to successively change the slice position of the sectional images 70 of the left and right breast being displayed on the display section 56 (namely, desires to successively change the sectional images 70), the user touches either the left or right breast sectional image 70, and moves so as to slide (move) the sectional image 70 to instruct the slice position so as to be changed successively. Whether to successively change the slice position in the direction such that the sectional image becomes deeper, namely, to successively change in the direction that the slice position becomes deeper (smaller), or to successively change in the direction such that the section image becomes shallower (higher), may be predetermined according to the direction in which the sectional image 70 was slid. In the present exemplary embodiment, as a specific example, in cases of sliding (the finger of the user) upward and toward the left from the state of the sectional images 70 indicated in FIG. 6, the slice position is successively changed in the direction that makes the slice position shallower (higher), and in cases of sliding downward and toward the right, the slice position is successively changed in the direction to become deeper (smaller).

A standby state is adopted in cases in which there is no successive change in slice position instructed, and the sectional images 70 continue to be displayed as they are. In cases in which the operation input detection section 58 detects the above movement (sliding), the controller 50 of the portable data terminal device 20 transitions to step S104.

At step S104, the slice position of the sectional images 70 being displayed on the display section 56 is changed successively, however, in the portable data terminal device 20 according to the present exemplary embodiment, the slice position of the one sectional images 70 on which successive slice position change was instructed (as a specific example, the sectional image 70L) is successively changed (the sectional image 70L is switched), and coupled to this, the display of the other sectional image 70 (as a specific example, the sectional image 70R) is switched to a combined sectional image (described in detail below).

Thus in the controller 50 according to the present exemplary embodiment, processing is performed to switch display of the one sectional image 70 (70L) that was instructed to be changed successively, and parallel processing is performed of processing for switching display of the other sectional image 70 (70R) and the combined sectional image.

In cases in which successive change of the one sectional image 70L has been instructed, at step S104A, the controller 50 successively switches the slice position of the sectional images 70L and displays the sectional images 70L. For example, in cases in which the slice position has been instructed to successively change in the direction to become shallower (higher) from the sectional image 70L with slice position 0 mm, the controller 50 reads out the sectional image 70L at the corresponding slice position from the sectional images 70L stored in the storage section 52, and sequentially switches the sectional image 70L being displayed on the display section 56 according to the successive change instruction, from the sectional image 70L with slice position 0 mm, through the sectional image 70L with slice position at 10 mm, to the sectional image 70L with slice position 20 mm.

However, for the other sectional image 70R, at step S104B, the controller 50 generates a combined sectional image according to the slice position of the sectional image 70L, and, coupled to the switching of the sectional image 70L, switches display of the combined sectional image that has been combined.

Explanation follows regarding the combined sectional image of the present exemplary embodiment, and generation of the combined sectional image. As described above, in cases in which the number of frames of the sectional images 70 of the left and the right breasts are different from each other, the switching timings of the sectional images 70 falls out of synchronization with each other. For example, in sectional images 70 illustrated in FIG. 5, since there are more frames of the sectional images 70L, in order to match the display of the sectional images 70R to the display (slice positions) of the sectional images 70L, there are cases in which the numbers of frames of the sectional images 70L and the sectional images sectional images 70R are made to align with each other during display by repeating display of the sectional image 70R having a particular slice thickness. For example, there is a case in which the sectional image 70R having a slice thickness of 30 mm is displayed twice, coupled to the sectional image 70L having a slice thickness of 30 mm and the sectional image 70L having a slice thickness of 40 mm. In the opposite scenario, in cases in which the sectional image 70L is to be displayed matched to display of the sectional image 70R (slice position), then the number of frames of the sectional images 70L and the sectional images 70R can be aligned by skipping (not displaying) the sectional image 70L having one particular slice thickness. There is, for example, a case in which display is performed while skipping the sectional image 70L at the slice thickness of 40 mm. In such circumstances, display of the sectional images 70 being switched becomes intermittent display, and sometimes display ceases to be viewed smoothly, such as in a case in which the speed of display change ceases to be constant.

In contrast thereto, in the controller 50 of the portable data terminal device 20 of the present exemplary embodiment, control is performed to make the display appear smooth as seen by a user by generating and displaying a combined sectional image of the other sectional image 70 (70R) to correspond to the slice position of the one sectional image 70 (70L) for which successive change in slice position has been instructed.

Figure 7:
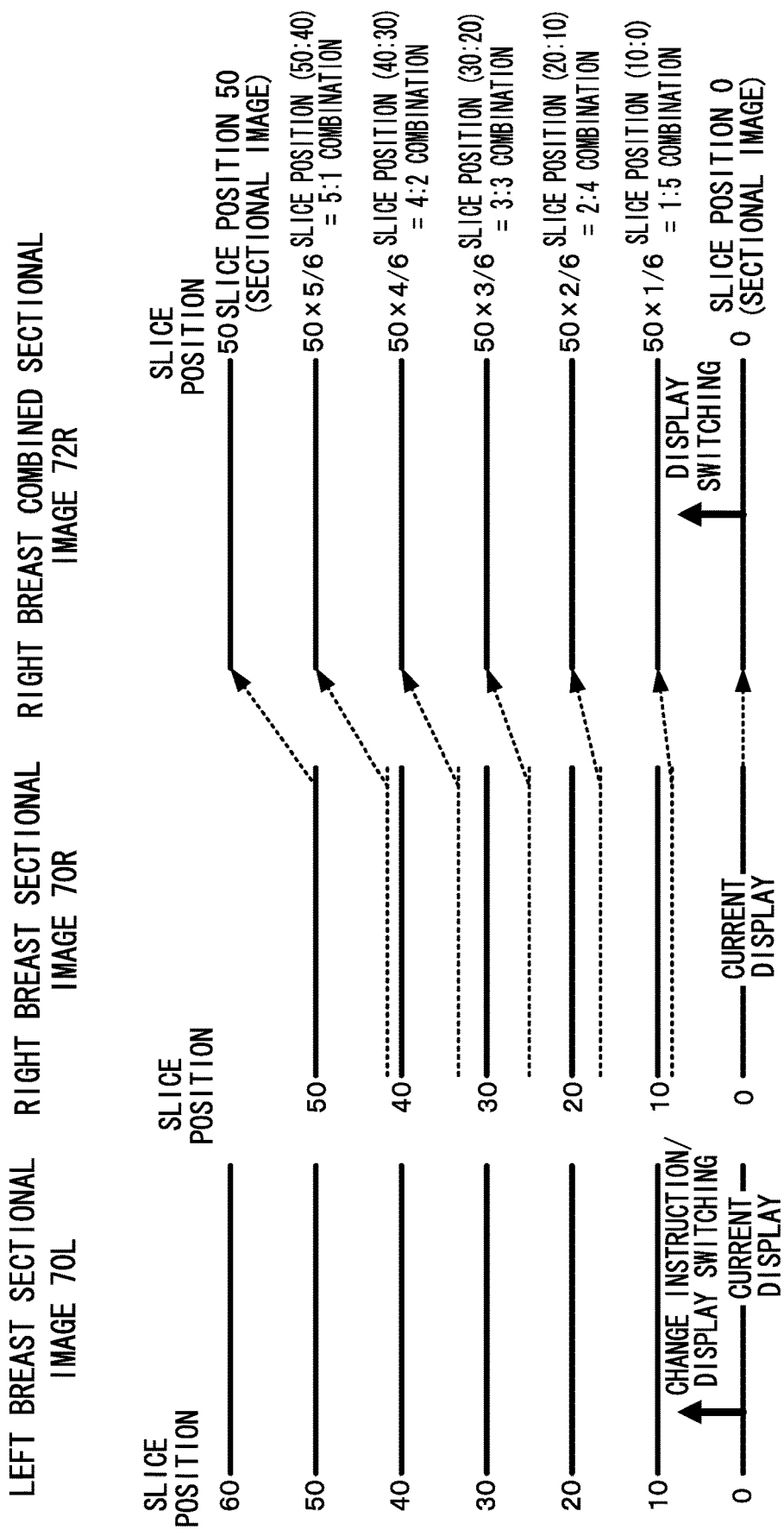
FIG. 7 is an explanatory diagram to explain generation of a combined sectional image by a controller of a portable data terminal device of the first exemplary embodiment.

FIG. 7 is an explanatory diagram to explain generation of the combined sectional image in the controller 50 of the portable data terminal device 20 of the present exemplary embodiment. In the controller 50 of the present exemplary embodiment, in order to make display smooth, the number of frames of the one sectional image 70L is made to effectively match the number of frames of the other sectional image 70R, by generating a combined sectional image 72R of the sectional images 70R corresponding to the slice position of the one sectional image 70L that was instructed to change successively.

In the controller 50 of the present exemplary embodiment, the pairs of sectional images 70 are pairs that have corresponding maximum values and minimum values of slice thickness. Thus there is no generation of a combined sectional image 72R corresponding to a maximum value or a minimum value of slice thickness.

As illustrated in FIG. 7, in cases in which the slice position displayed on the display section 56 is currently successively changing from the sectional image 70 of the slice position 0 mm in the direction in which the slice position becomes shallower (higher), the controller 50 generates combined sectional images 72R corresponding to each of the slice positions of the sectional image 70L, at 10 mm, 20 mm, 30 mm, 40 mm, and 50 mm.

The method of generation is combination from 2 frames of sectional image 70R close to the slice position of the sectional image 70L (namely positioned in the depth direction above/below the slice position of the sectional image 70L), at a proportion according to the slice positions of the 2 frames. Namely, generation is a combination from 2 frames of sectional image 70R, according to a weighted average according to the slice positions of the 2 frames.

In the specific example illustrated in FIG. 7, the sectional image 70R with slice position at 10 mm and the sectional image 70R with slice position at 0 mm are combined at a ratio of 1:5, to effectively generate a combined sectional image 72R with slice position at 50×⅙ mm corresponding to the sectional image 70L with slice position at 10 mm. Similarly, the sectional image 70R with slice position at 20 mm and the sectional image 70R with slice position at 10 mm are combined at a ratio of 2:4, to effectively generate a combined sectional image 72R with slice position at 50×²⁄₆ mm corresponding to the sectional image 70L with slice position at 20 mm. The sectional image 70R with slice position at 30 mm and the sectional image 70R with slice position at 20 mm are combined at a ratio of 3:3, to effectively generate a combined sectional image 72R with slice position at 50×³⁄₆ mm corresponding to the sectional image 70L with slice position at 30 mm. The sectional image 70R with slice position at 40 mm and the sectional image 70R with slice position at 30 mm are combined at a ratio of 4:2, to effectively generate a combined sectional image 72R with slice position at 50×⁴⁄₆ mm corresponding to the sectional image 70L with slice position at 40 mm. Moreover, the sectional image 70R with slice position at 50 mm and the sectional image 70R with slice position at 40 mm are combined at a ratio of 5:1, to effectively generate a combined sectional image 72R with slice position at 50×⅚ mm corresponding to the sectional image 70L with slice position at 50 mm.

Figure 8:
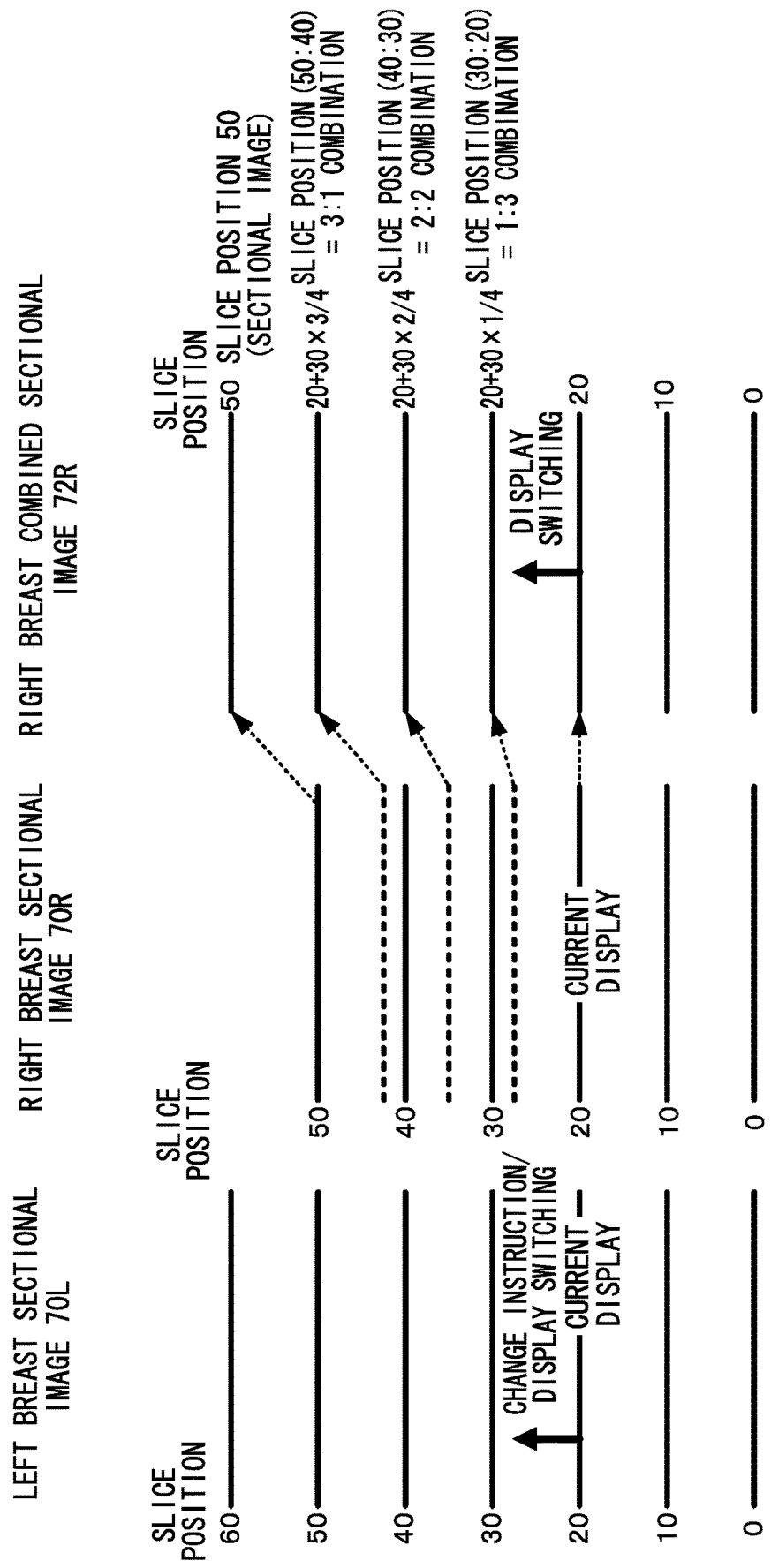
FIG. 8 is an explanatory diagram to explain generation of a combined sectional image by a controller of a portable data terminal device of the first exemplary embodiment.

On receipt of an instruction to successively change the slice position of the one sectional image 70L, the controller 50 of the present exemplary embodiment generates the combined sectional images 72R as described above for the other sectional images 70R. In cases in which there is a continuous instruction to successively change, such as cases in which the user continues sliding the sectional images 70L displayed on the display section 56, due to it being unclear which is the slice position of the sectional image 70L to finally be displayed, the controller 50 preferably generates (including sequentially generates) combined sectional images 72R corresponding to all conceivable slice positions as the change destination from the slice position of the currently displayed sectional image 70L. FIG. 8 is an explanatory diagram to explain generation of combined sectional images in the controller 50 of the portable data terminal device 20 of the present exemplary embodiment. The specific example illustrated in FIG. 8 illustrates a case in which, in the state in which the sectional images 70 with slice positions at 20 mm are being displayed, instruction is made to successively change the slice position in the direction in which the slice thickness of the sectional image 70L becomes shallower (higher). In a case in which the controller 50 has recognized that there is a successive change in the direction in which the slice position successively changes (the direction making the slice position shallower/higher), then the controller 50 generates the combined sectional images 72R corresponding to each of the sectional images 70L at the slice positions 30 mm, 40 mm, and 50 mm. In the specific example illustrated in FIG. 8, the sectional image 70R with slice position at 30 mm and the sectional image 70R with slice position at 20 mm are combined at a ratio of 1:3, to effectively generate a combined sectional image 72R with slice position at 20+30×¼ mm corresponding to the sectional image 70L with slice position at 30 mm. Similarly, the sectional image 70R with slice position at 40 mm and the sectional image 70R with slice position at 30 mm are combined at a ratio of 2:2, to effectively generate a combined sectional image 72R with slice position at 20+30×²⁄₄ mm corresponding to the sectional image 70L with slice position at 40 mm. Moreover, the sectional image 70R with slice position at 50 mm and the sectional image 70R with slice position at 40 mm are combined at a ratio of 3:1, to effectively generate a combined sectional image 72R with slice position at 20+30×¾ mm corresponding to the sectional image 70L with slice position at 50 mm.

Namely, the controller 50 generates the combined sectional images 72R by combining 2 frames of sectional image 70R, at combination proportions corresponding to the slice position of the sectional image 70R currently being displayed, the final slice position in the change direction (having the highest value of lowest value), and the number of the combined sectional images 72R to be generated.

Thus the controller 50 generates the combined sectional images 72R, and then switches to displaying the combined sectional image 72R corresponding to the slice position of the sectional image 70L coupled to switching of display of the one sectional image 70L.

At the next step S106, the controller 50 determines whether or not instruction to successively change the slice position has ended. For example, in cases in which successive change continues to be instructed, such as by a user continuing sliding on the sectional image 70L, the processing of step 104 (S104A, S104B) is repeated. However, for example, in cases in which there is no sliding (movement) on the sectional image 70L for a fixed period of time or longer, or the user is not touching the display section 56, determination is made that the instruction to successively change has ended, and processing proceeds to step S108.

At step S108, the controller 50 switches display of the other sectional image 70R to displaying the sectional image 70R having a slice position that is closest in the depth direction to the slice position of the one sectional image 70L after the change. In a state in which instruction to change the slice position successively has ended, for example in the specific case illustrated in FIG. 7 in which the slice position of the one sectional image 70L has changed to 40 mm, the left breast is displayed on the display section 56 in a state in which the one sectional image 70L with slice position at 40 mm is displayed. Whereas, the right breast is displayed in a state in which the combined sectional image 72R combined from the sectional image 70R with slice position at 40 mm and the sectional image 70R having the slice position at 30 mm, at the ratio 4:2. Thus, at the present step, as illustrated in the specific example of FIG. 9, the controller 50 switches display of the right breast from the combined sectional image 72R to the sectional image 70R having the slice position at 40 mm.

Thus by switching display on the other side from the combined sectional image 72R to the sectional image 70R, the left and right breasts are displayed on the display section 56 in a state in which the sectional images 70 have corresponding slice positions.

At the next step S110, determination is made as to whether or not to end the current processing. For example, in cases such as those in which display of the sectional images 70 on the display section 56 continues to be performed, determination is made to not end the processing, processing returns to step S102, and the current processing is repeated. However, for example, in a case in which an instruction to end display of the sectional image 70 has been received by the operation input detection section 58, the current processing is ended.

Figure 10:
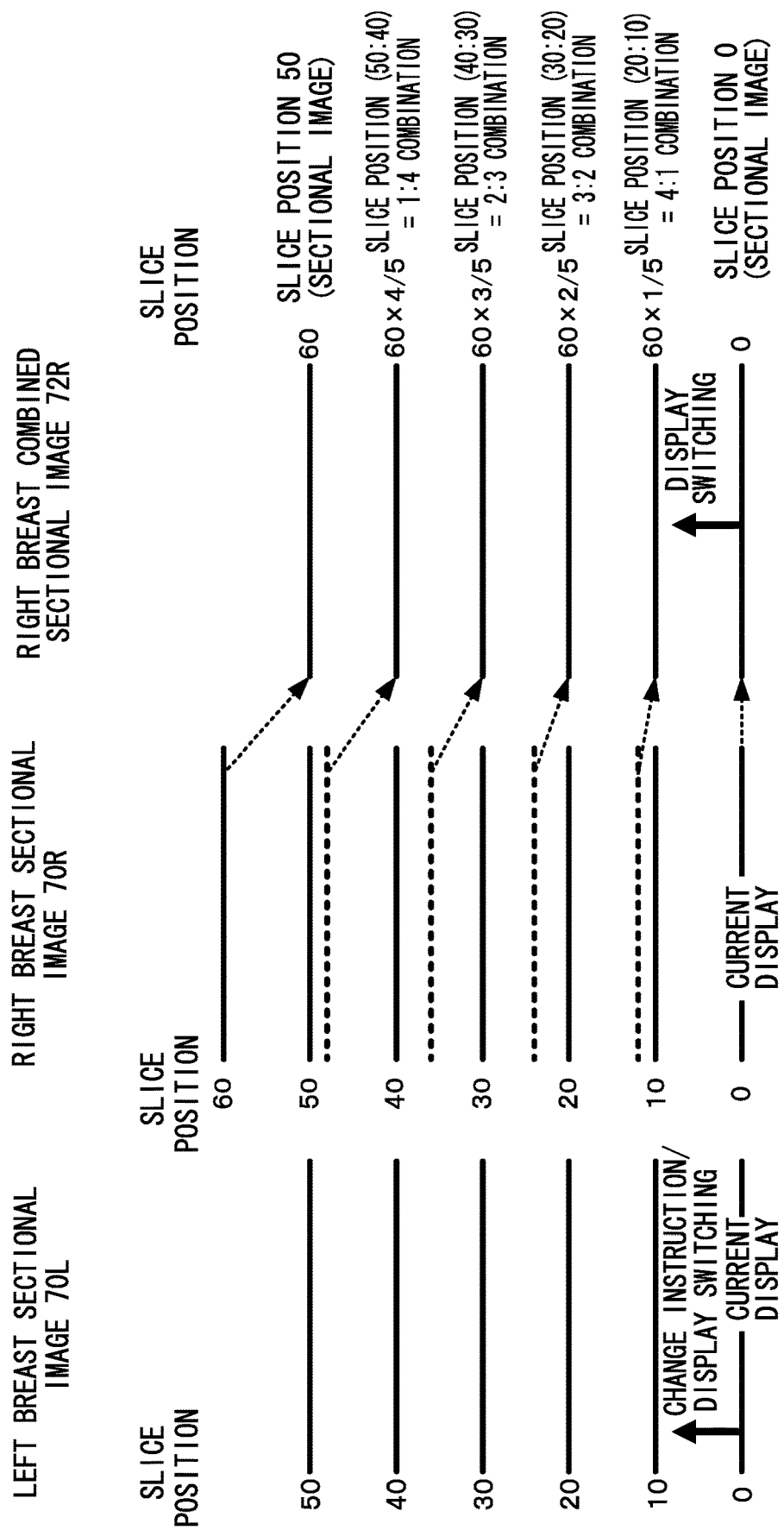
FIG. 10 is an explanatory diagram to explain generation of a combined sectional image by a controller of a portable data terminal device of a first exemplary embodiment.

As described above, explanation has been given of a case in which there are more frames of the sectional images 70L than of the sectional images 70R. However, similarly in cases in which there are fewer frames of the sectional images 70L than of the sectional images 70R, the controller 50 may generate the combined sectional image 72R and switch display coupled to switching the slice position of the one sectional image 70L. FIG. 10 is an explanatory diagram to explain generation of combined sectional images 72R by the controller 50 in such a case. The specific example illustrated in FIG. 10, similarly to the specific example illustrated in FIG. 7, illustrates a case in which instruction has been made to successively change the slice position, from the slice position at 0 mm, in the direction becoming shallower (higher).

In the specific example illustrated in FIG. 10, the sectional image 70R with slice position at 20 mm and the sectional image 70R with slice position at 10 mm are combined at a ratio of 4:1, to effectively generate a combined sectional image 72R with slice position at 60×1/5 mm corresponding to the sectional image 70L with slice position at 10 mm. Similarly, the sectional image 70R with slice position at 30 mm and the sectional image 70R with slice position at 20 mm are combined at a ratio of 3:2, to effectively generate a combined sectional image 72R with slice position at 60×2/5 mm corresponding to the sectional image 70L with slice position at 20 mm. The sectional image 70R with slice position at 40 mm and the sectional image 70R with slice position at 30 mm are combined at a ratio of 2:3, to effectively generate a combined sectional image 72R with slice position at 60×3/5 mm corresponding to the sectional image 70L with slice position at 30 mm. Moreover, the sectional image 70R with slice position at 50 mm and the sectional image 70R with slice position at 40 mm may be combined at a ratio of 1:4, to effectively generate a combined sectional image 72R with slice position at 60×4/5 mm corresponding to the sectional image 70L with slice position at 40 mm.

Second Exemplary Embodiment

In the first exemplary embodiment, in cases in which the controller 50 of the portable data terminal device 20 has received an instruction to successively change the slice position of the one sectional image 70L, the one sectional image 70L is switched according to successive changes to the slice position, and coupled to this switching, switching is performed to switch to displaying the combined sectional image 72R of the other sectional image 70R corresponding to the slice position of the one sectional image 70L. In the present exemplary embodiment, switching of the combined sectional image 72R will be referred to as "fading".

Explanation follows regarding of the present exemplary embodiment in which, in addition to fading as explained with respect to the first exemplary embodiment, the controller 50 has also been instructed to successively change the slice position with respect to the one sectional image 70L.

For the one sectional image 70L, the controller 50 of the portable data terminal device 20 may, similarly to step S104A of the first exemplary embodiment, successively switch the slice position of the sectional image 70L and display the switched-slice-position sectional image 70L.

Figure 11:
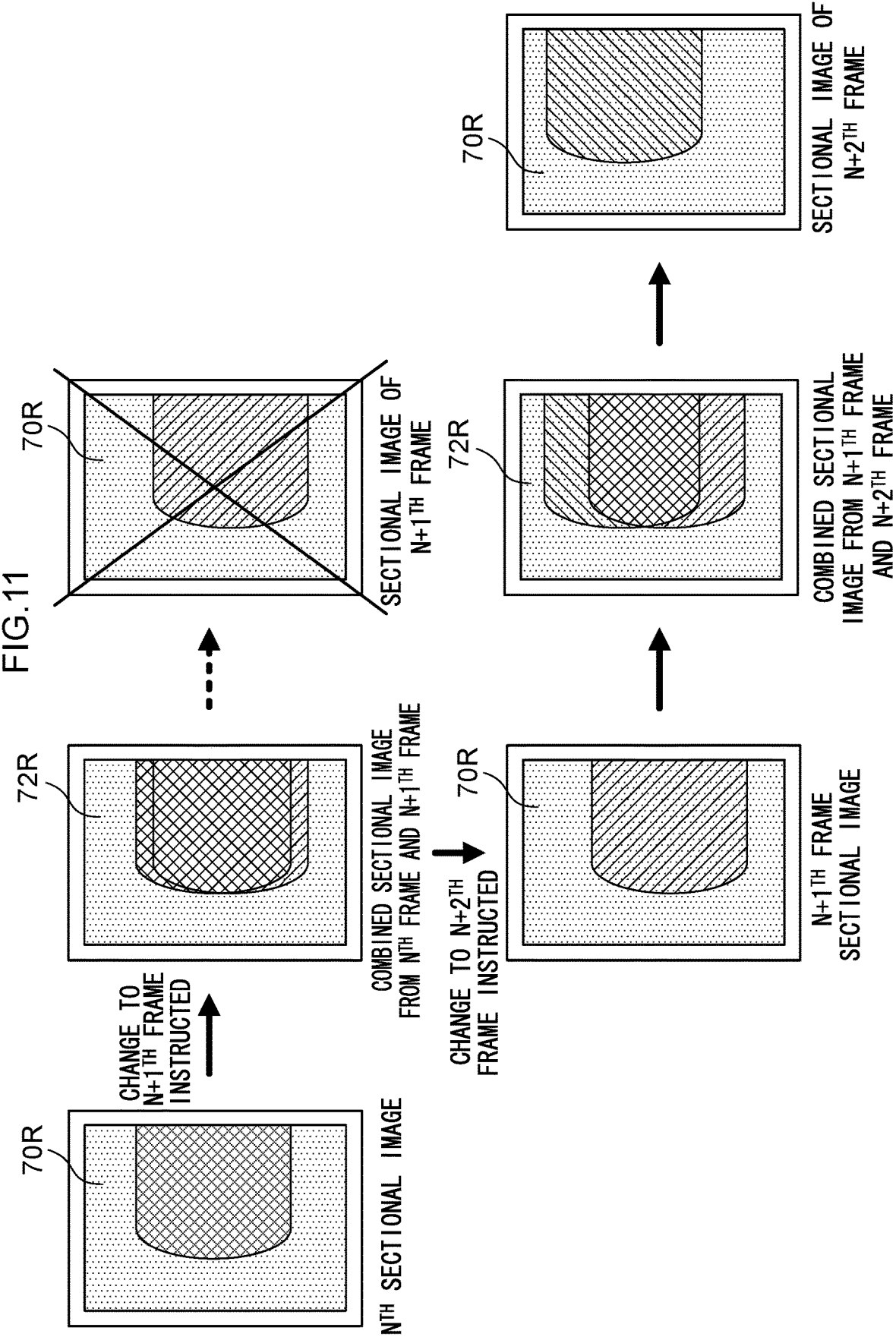
FIG. 11 is an explanatory diagram to explain an example of switching of the other sectional image in a case in which a change in slice position is instructed during fading.

For the other sectional image 70R, the controller 50 of the portable data terminal device 20 performs different processing in the present exemplary embodiment to that of the first exemplary embodiment. FIG. 11 is an explanatory diagram to explain an example of switching the other sectional image 70R in cases in which successive change to the slice position has been instructed during fading. FIG. 11 illustrates a case in which an $N^{th}$ frame (an example of a sectional image in a first slice position) of the sectional images 70R is being displayed, successive change of the slice position to change to an $N+2^{th}$ frame (an example of a sectional image of a third slice position) is instructed during fading to an $N+1^{th}$ frame (an example of a sectional image in the second slice position) instructed for a successive change of the slice position. For transition from the $N^{th}$ frame sectional image 70R to the $N+1^{th}$ frame sectional image 70R, the controller 50 generates a combined sectional image 72R combined from the $N^{th}$ frame and the $N+1^{th}$ frame, and displays the combined sectional image 72R. During generation of the combined sectional image 72R or the like, in cases in which successive change to the slice position is instructed during fading, the current fading is stopped. The controller 50 then first displays the sectional image 70R corresponding to the previous change destination slice position (the final change position) on the display section 56 (the $N+1^{th}$ frame sectional image 70R in the case illustrated in FIG. 11). Then, the controller 50 generates a combined sectional image 72R from the $N+1^{th}$ frame slice position according to the newly instructed change destination slice position, similarly to step S104B of the first exemplary embodiment, and displays the combined sectional image 72R. The controller 50 accordingly fades to a combination of the N+1$^{th}$ frame sectional image 70R and the N+2$^{th}$ frame sectional image 70R.

Figure 12:
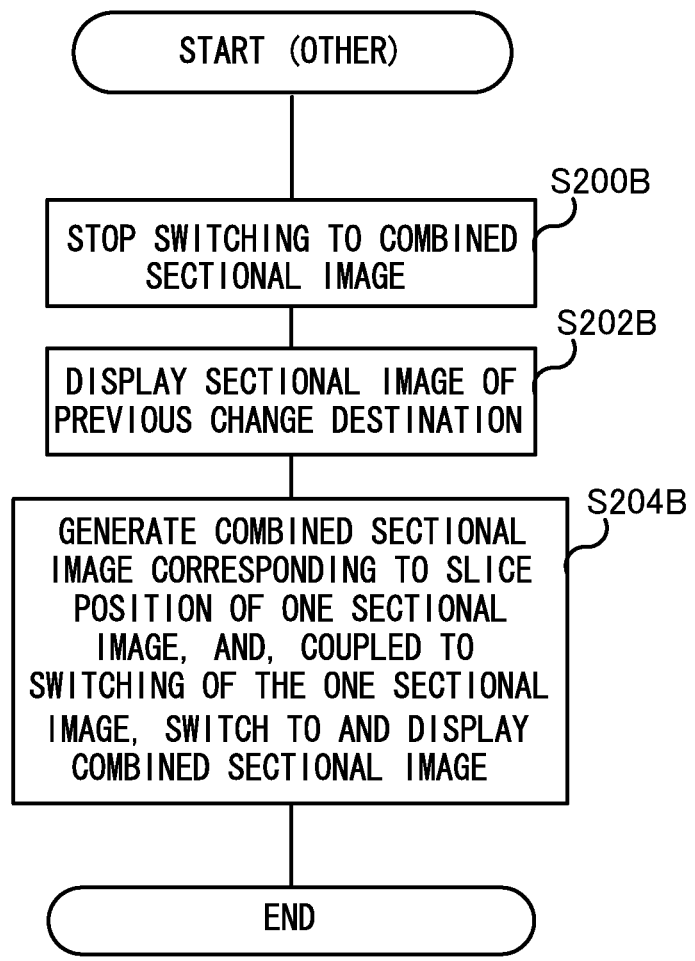
FIG. 12 is a flowchart of sectional image display processing of the other sectional image in a case in which a change in slice position is instructed during fading.

FIG. 12 is a flowchart illustrating an example of sectional image display processing for the other sectional image 70R in cases in which successive change of the slice position is instructed during fading.

At step S200B, the controller 50 switches to the combined sectional image 72R, namely ends fading. Then at step S202B, the controller 50 first displays the sectional image 70R corresponding to the slice position of the previous change destination on the display section 56. In the specific example illustrated in FIG. 7, in a case in which successive change to the slice position of 60 mm is instructed during fading from the slice position 0 mm to the slice position at 20 mm, at step S202B, the controller 50 first displays the sectional image 70R at the slice position of 20 mm on the display section 56.

Then at the next step S204B, the controller 50 generates a combined sectional image 72R, similarly to at step S104B of the first exemplary embodiment, and ends the current processing after displaying the combined sectional image 72R. In the above example, as illustrated in FIG. 8, the controller 50 generates the combined sectional image 72R, and performs switching to display the combined sectional image 72R.

In this manner, in cases in which new instruction is made to successively change the slice position of the one sectional image 70L during fading of the other sectional image 70R, the fading is temporarily interrupted, the new combined sectional image 72R is generated, and switching is performed to display the new combined sectional image 72R. Thereby misalignment between the left and right slice positions is suppressed, and the sectional images 70 of the left and right breasts being displayed on the display section 56 are coupled together for switching.

The sectional image display processing of the sectional image 70R in cases in which successive change to the slice position is additionally instructed for the one sectional image 70L during fading is not limited to the specific examples illustrated in FIG. 11 and FIG. 12. Explanation follows regarding other specific examples.

Figure 13:
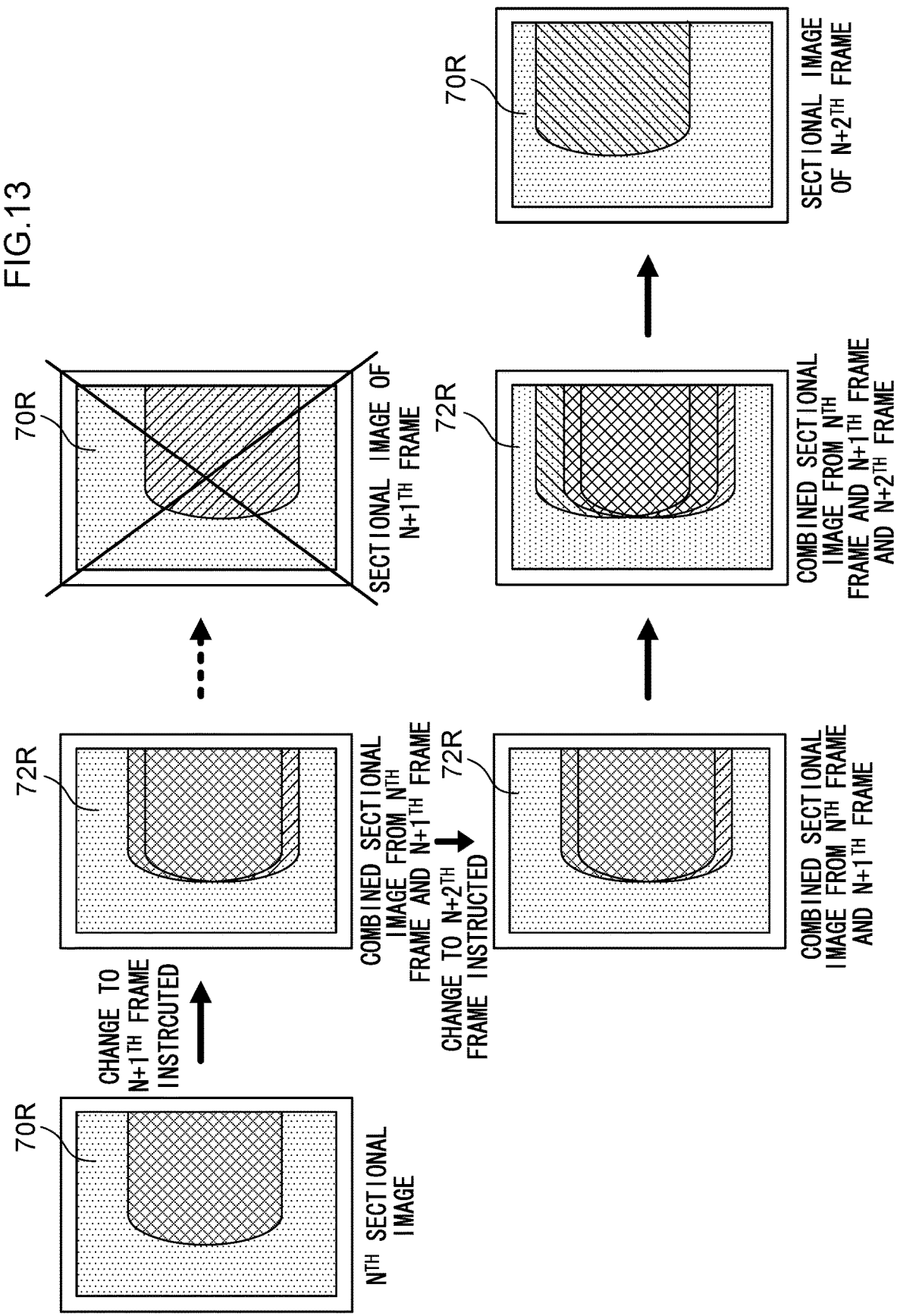
FIG. 13 is an explanatory diagram to explain another example of switching of the other sectional image in a case in which a change in slice position is instructed during fading.

FIG. 13 is an explanatory diagram to explain another example of switching the other sectional image 70R in cases in which successive change to the slice position is instructed during fading. FIG. 13 illustrates a case in which the N$^{th}$ frame (an example of a sectional image in a first slice position) sectional image 70R is being displayed, successive change of the slice position to change to an N+2$^{th}$ frame (an example of a sectional image of a third slice position) is instructed during fading to an N+1$^{th}$ frame (an example of a sectional image in the second slice position) instructed for a successive change of the slice position. During transition from the N$^{th}$ frame sectional image 70R to the N+1$^{th}$ frame sectional image 70R, the controller 50 generates and displays a combined sectional image 72R combined from the N$^{th}$ frame and the N+1$^{th}$ frame. In cases in which during fading, such as during generation of the combined sectional image 72R, successive change to the slice position is instructed, the current fading is stopped. The controller 50 then, similarly to at step S104B of the first exemplary embodiment, generates and displays a new combined sectional image 72L according to the slice position corresponding to the combined sectional image 72R currently being displayed, or being generated, and the newly instructed slice position. The controller 50 accordingly generates a new combined sectional image 72R by combining the combined sectional image 72R, combined using the N$^{th}$ frame sectional image 70R and the N+1$^{th}$ frame sectional image 70R, and the N+2$^{th}$ frame sectional image 70R, and starts the fading.

Figure 14:
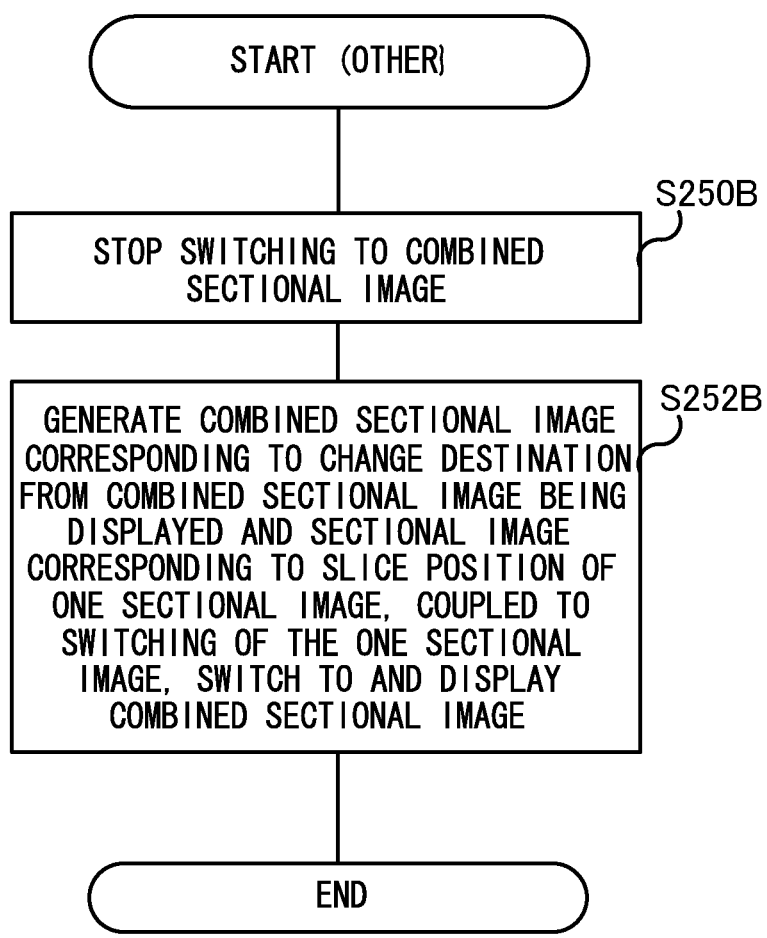
FIG. 14 is a flowchart of another example of sectional image display processing of the other sectional image in a case in which a change in slice position is instructed during fading.

Moreover, FIG. 14 illustrates a flowchart of another example of sectional image display processing for the other sectional image 70R in cases in which successive change to the slice position is instructed during fading.

At step S250B, the controller 50 switches to the combined sectional image 72R, namely stops fading.

Then at step S252B, similarly to at step S104B of the first exemplary embodiment, the controller 50 generates and displays a new combined sectional image 72L according to the slice position corresponding to the combined sectional image 72R and the newly instructed slice position, and then ends the current processing. In the specific example illustrated in FIG. 7, in cases in which successive change is instructed during fading from the combined sectional image 72R corresponding to the slice position at 0 mm to the combined sectional image 72R corresponding to the slice position at 20 mm, the controller 50 calculates a new combination proportion between the current slice position at 20 mm and the newly instructed slice position, generates a new combined sectional image 72R combined from the combined sectional image 72R of the slice position at 20 mm, and the sectional image 70R at the calculated combination proportion, and displays the new combined sectional image 72R on the display section 56. The controller 50 then sequentially a combines the combined sectional images 72R that were combined from the sectional image 70R at the new combination proportion, and switches to displaying the combined sectional image 72R coupled to switching of the sectional image 70L.

In this manner, in cases in which a new instruction is given to successively change the slice position of the one sectional image 70L during fading of the other sectional image 70R, the new combination proportion is calculated according to the slice position of the combined sectional image 72R during fading, and the combined sectional image 72R is generated according to the calculated combination proportion. Thereby the sectional images 70 of the left and right breasts are displayed on the display section 56 while suppressing misalignment between the left and right slice positions, and coupled switching is performed of the left and right sectional images 70.

In the above, in the radiographic imaging system 10 of each of the exemplary embodiments explained above, the controller 30 of the console 16 generates the left and right pair of sectional images 70 of the breasts from the radiographic images imaged by the radiation detector 22 of the radiographic imaging device 12, and transmits the generated sectional images 70 to the portable data terminal device 20. The controller 50 of the portable data terminal device 20 displays the pair of sectional images 70 on the display section 56. The controller 50 switches the one sectional image 70L according to successive change to the slice position in cases in which instruction is received to successively change the slice position of the one sectional image 70L, and coupled to this switching, the combined sectional image 72R of the other sectional image 70R is generated according to the slice position of the one sectional image 70L, and switching is performed to display the generated combined sectional image 72R. The combined sectional image 72R is generated by combining from the two frames of the sectional image 70R close to the slice position in the depth direction (namely, positioned above/below in the depth direction).

In cases in which pairs of mutually related sectional images 70 are displayed due to the controller 50 generating the combined sectional image 72R in this manner, and switching display coupled to switching the sectional image 70L, display of the other sectional image 70R can be switched smoothly, as if animated, coupled to switching of the slice position of the one sectional image 70L.

Figure 15:
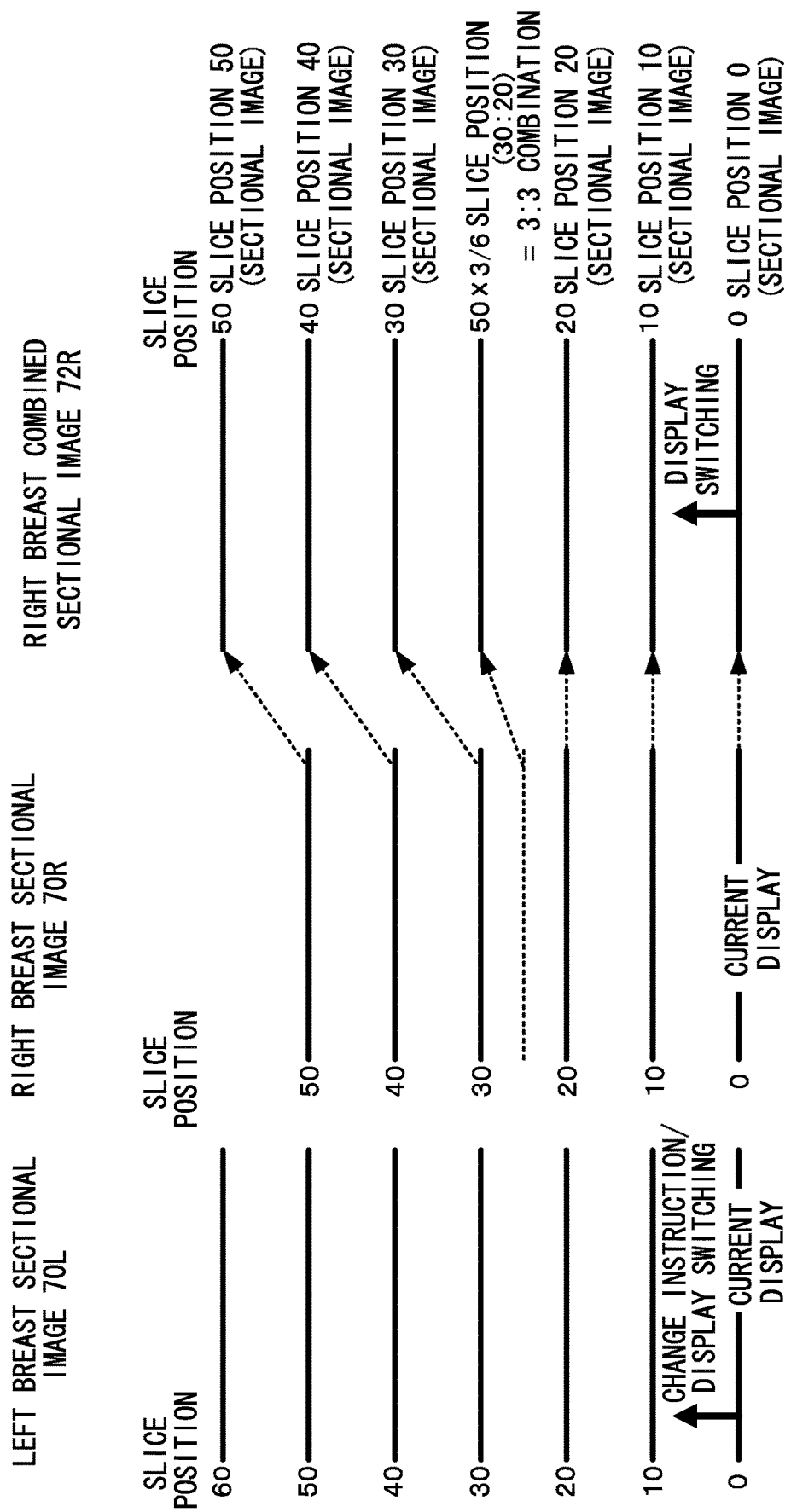
FIG. 15 is an explanatory diagram to explain a specific example of generating a combined sectional image.

Explanation has been given in each of the above exemplary embodiments of cases in which the controller 50 generates the combined sectional image 72 according to the other slice positions, except for the greatest value and the smallest value of slice thickness of the one sectional image 70L, however the combined sectional images 72 are not necessarily combined so as to correspond to all the slice positions. A specific example of combined sectional images 72 in such a case is illustrated in FIG. 15. In the controller 50 of each of the above exemplary embodiments, the number of frames of the sectional image 70L and the number of frames of the sectional images 70R (including the combined sectional images 72) match each other. Thus configuration may be made such that combined sectional images 72R are only generated to correspond to the missing number of frames. The specific example illustrated in FIG. 15 illustrates an example in which only the combined sectional image 72R is generated corresponding to the sectional image 70L with slice position at 30 mm by combining the sectional image 70R at the slice position at 30 mm and the sectional image 70R at the slice position at 20 mm at a combination proportion of 3:3, and for the other sectional images switching is performed to display using the sectional images 70R.

Explanation has been given in each of the above exemplary embodiments of cases in which the number of frames of the sectional images 70 of the left and right breasts are made to substantially match. However, the number of frames of the sectional images 70 of the left and right breasts need not necessarily match, and in particular the effective number of frames of the other sectional image 70R may be made greater than the one sectional image 70L. In such cases, a new slice position may be provided between the existing slice positions of the sectional image 70L, and a combined sectional image 72R corresponding to the provided slice positions may be generated and displayed. In this manner, display of the other sectional image 70R can be made to change smoothly, gradually as if animated, by making the effective number of frames of the other sectional image 70R greater than the sectional image 70L.

Figure 16:
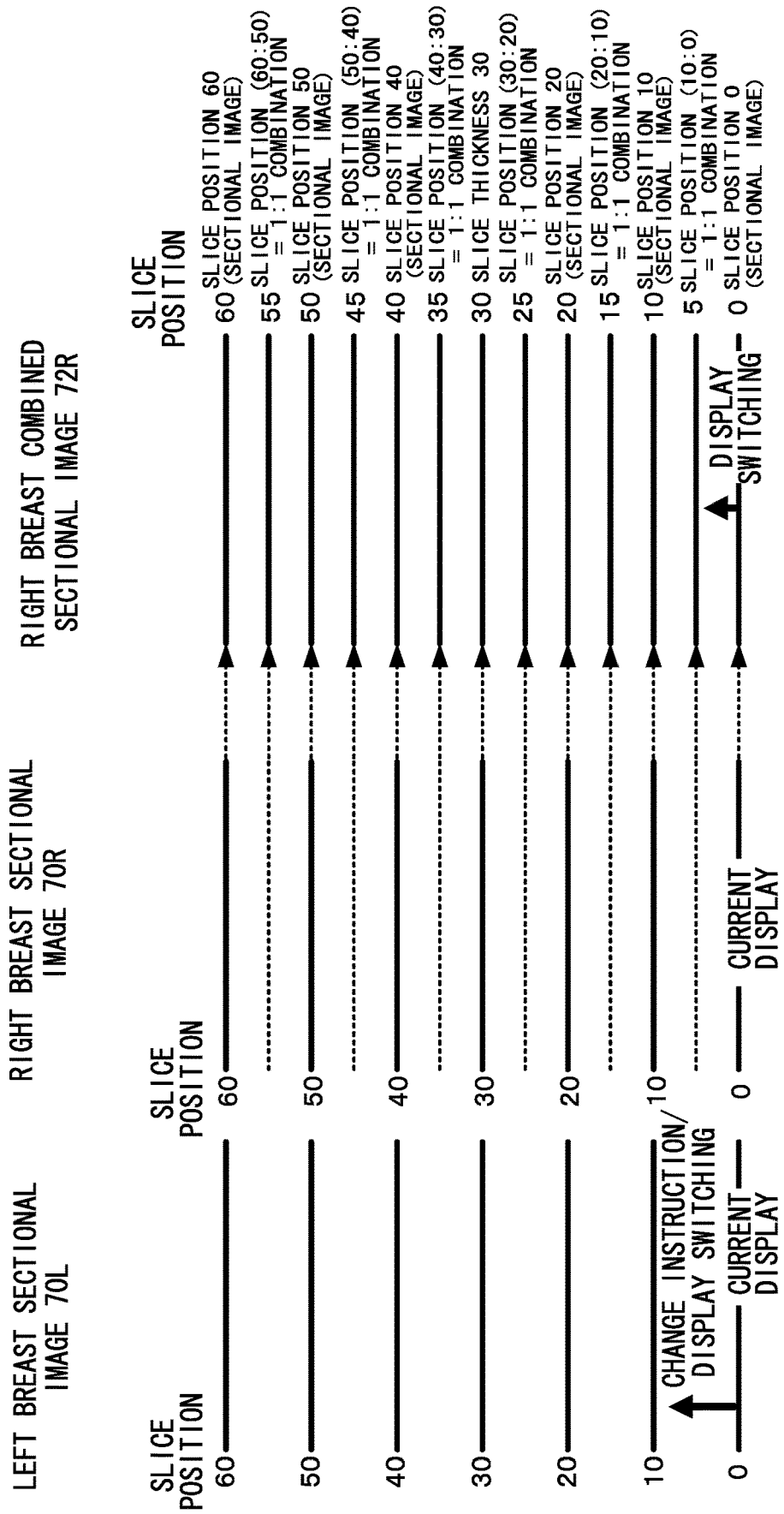
FIG. 16 is an explanatory diagram to explain a specific example of generating a combined sectional image.

Moreover, although in each of the above exemplary embodiments cases have been explained in which the number of frames of the sectional images 70 of the left and right breasts are different from each other, similarly, even there are the same number of frames, as in a specific example, the effective number of frames generated of the combined sectional images 72R for the other sectional image 70R may be greater than those of the one sectional image 70L. In the specific example illustrated in FIG. 16, a new slice position is provided between the existing slice positions of the sectional image 70R, and a combined sectional image 72R corresponding to the provided slice position may be generated and displayed. In a specific example illustrated in FIG. 16, this results in display on the other side being performed by switching alternately between display of the combined sectional image 72R, or the sectional image 70R, according to the slice position.

Figure 17:
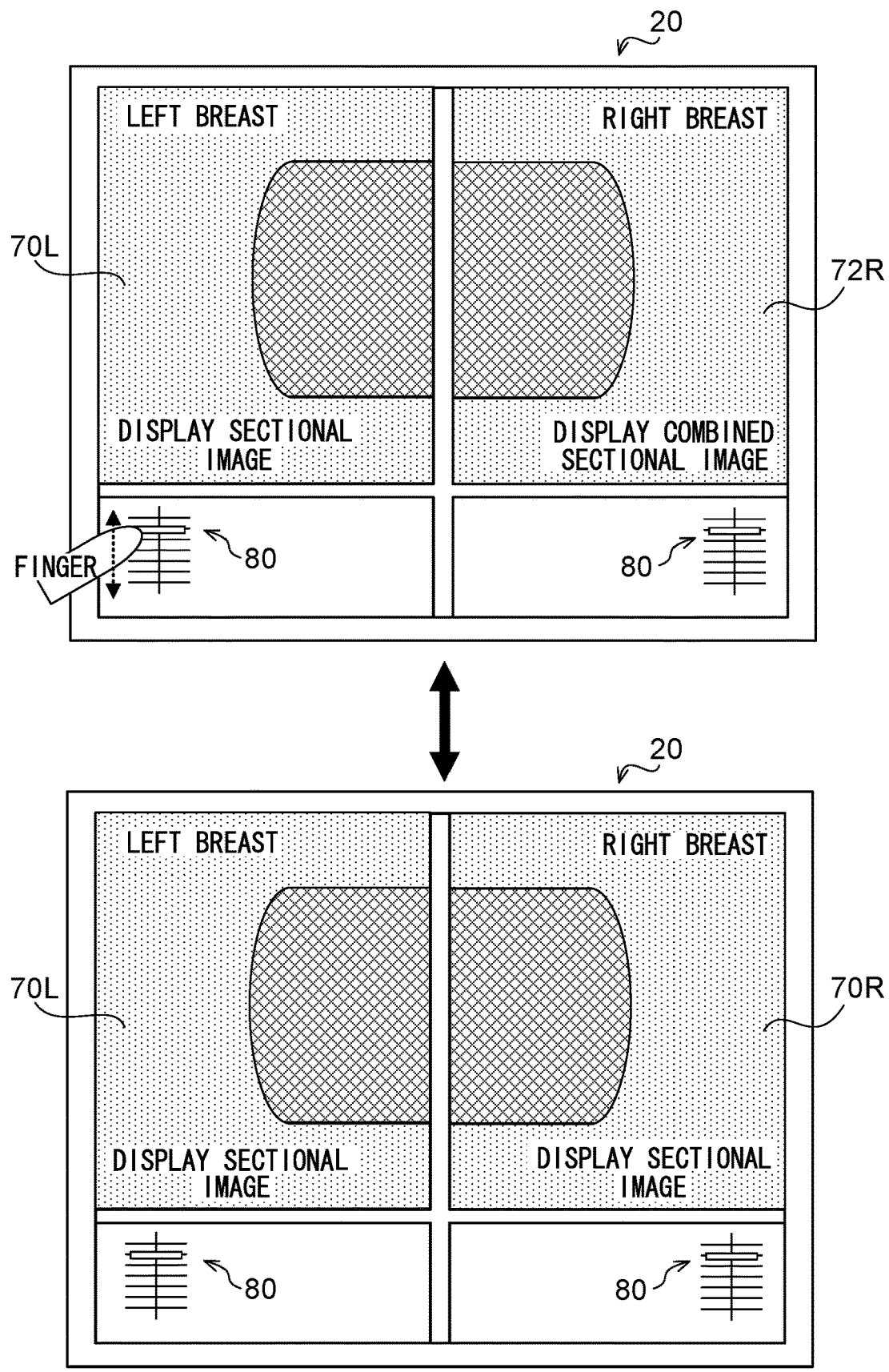
FIG. 17 is an explanatory diagram to explain a specific example of generating a combined sectional image.

Explanation has been given in each of the above exemplary embodiments of cases in which successive change of the slice position is instructed by a user operating (sliding etc.) on the sectional image 70 being displayed on the display section 36 of the portable data terminal device 20, however the method of instructing successive change to the slice position is not limited thereto. For example, as illustrated in FIG. 17, in cases in which a bar 80 or the like has been displayed on the display section 36 as a display to represent the slice position (depth), the controller 50 may instruct successive change to the slice position by a user operating the bar 80 with a finger, or operating the operation section 60.

Moreover, although explanation has been given of cases in each of the above exemplary embodiments in which the controller 50 of the portable data terminal device 20 generates the combined sectional image 72 after receiving an instruction to perform successive change of the slice position, there is no limitation to the timing to generate the combined sectional image 72. In advance, combined sectional images 72 of both breasts may be generated according to slice positions (number of frames) of the sectional images 70 of both breasts, and stored in the storage section 52.

Figure 18:
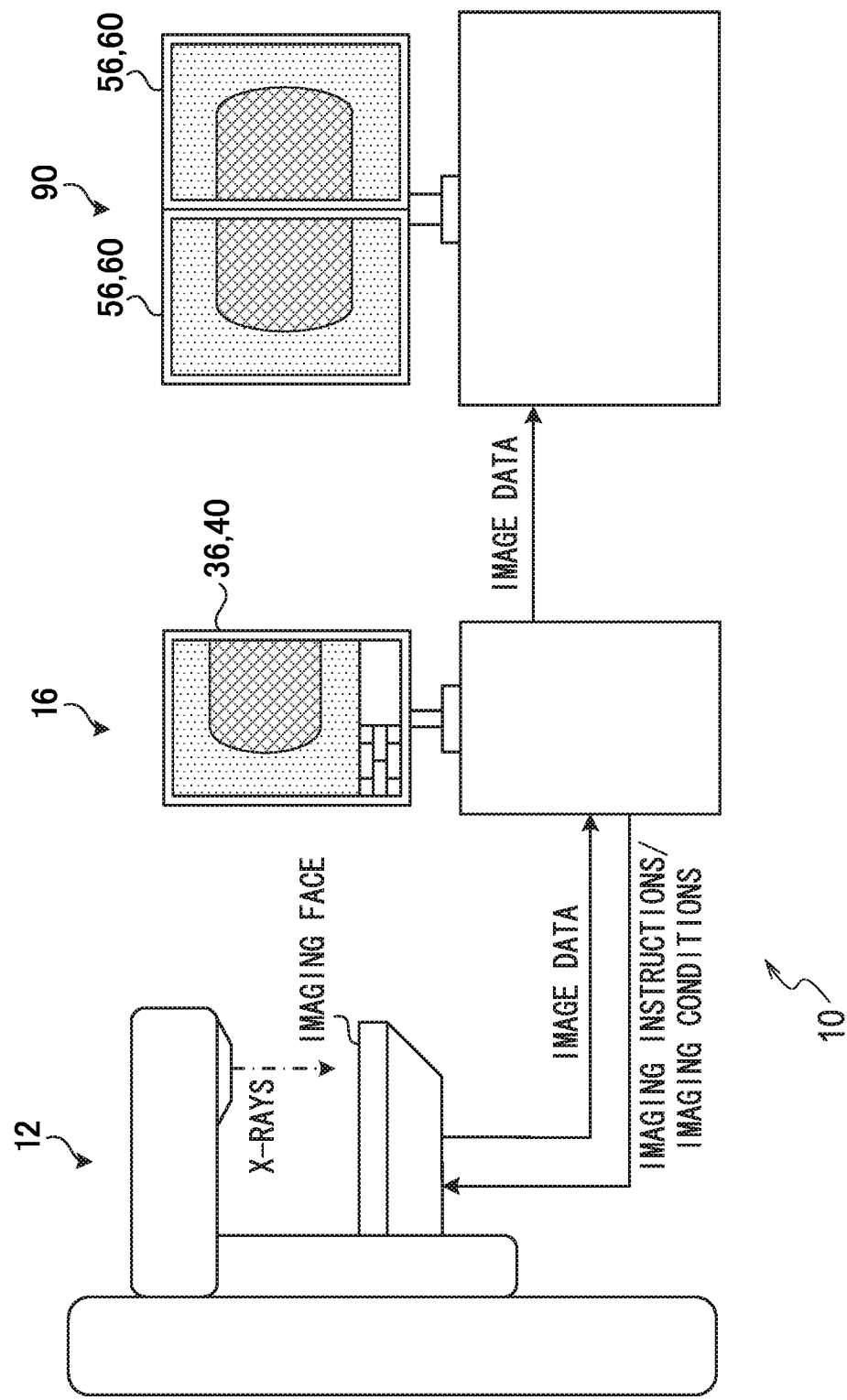
FIG. 18 is a schematic configuration diagram illustrating an outline overall configuration of a radiographic imaging system in a case in which a viewer is provided as a radiographic image reading device instead of a portable data terminal device.

Moreover, although explanation has been given in each of the above exemplary embodiments of cases in which the portable data terminal device 20 is a tablet terminal, the portable data terminal device 20 is not limited to being a tablet terminal. Moreover, there is no limitation to the portable data terminal device 20, and another radiographic image reading device may be employed, such as a viewer. FIG. 18 illustrates a schematic configuration diagram illustrating an overall schematic configuration of an example of a radiographic imaging system for a case in which a radiographic image reading device 90 is employed as a viewer instead of the portable data terminal device 20. Moreover, for example, another device may be employed instead of the portable data terminal device 20, such as an ordinary personal computer. FIG. 19 is a schematic configuration diagram illustrating an overall schematic configuration of an example of a radiographic imaging system for a case in which a device equivalent to a personal computer is provided instead of the portable data terminal device 20.

Explanation has been given in each of the above exemplary embodiments of cases in which the sectional images 70 are generated in the console 16, however the sectional images 70 may be generated in the portable data terminal device 20. Explanation has been given in each of the above exemplary embodiments of cases in which the controller 50 of the portable data terminal device 20 includes functionality of a generation section to generate the combined sectional images 72R, and includes functionality of a controller to switch the other combined sectional image 72R coupled to switching display of the one sectional image 70L, however there is no limitation thereto. For example, the controller 30 of the console 16 may include each of these functional sections, and then the portable data terminal device 20 may be dispensed with in cases in which the sectional images 70 are only displayed on the display section 36 of the console 16. Moreover, the controller 30 of the console 16 may include some of these functional sections, and the other functional sections may be included in the controller 50 of the portable data terminal device 20.

Moreover, explanation has been given in each of the above exemplary embodiments of case in which the sectional images 70 of the left and right breasts serve as an example of a pair of mutually related sectional images, however the pair of mutually related sectional images is not particularly limited. For example, the sectional images 70 may be of either the left or right breast, taken at different imaging times.

Moreover, explanation has been given of cases of the radiographic imaging system 10 of each of the above exemplary embodiments in which the radiographic imaging device 12 is a mammography device; however another radiographic imaging device may be employed. Moreover, the imaging target is also not limited to a breast, and may be another site, without particular limitation.

Moreover, explanation has been given in each of the above exemplary embodiments of cases in which successive change to the slice position of the left breast sectional image 70L was instructed as the one sectional image 70, however it is obvious that successive change to the slice position of the right breast sectional images 70R may be similarly instructed as the one sectional image 70.

Moreover, the radiation employed for imaging the radiographic images is not particularly limited, and X-rays, gamma-rays or the like may be suitably employed.

Configuration and operation of the radiographic imaging system 10, the radiographic imaging device 12, the console 16, and the portable data terminal device 20 as explained in each of the above exemplary embodiments are merely examples thereof, and obviously modifications may be made according to the circumstances, within a range not departing from the spirit of the present invention. Moreover, the flow of sectional image display processing explained in each of the above exemplary embodiments is merely an example, and obviously modifications may be made according to the circumstances, within a range not departing from the spirit of the present invention.

What is claimed is:

1. An image display device, comprising:
    a display that displays a pair of mutually related sectional images;
    a memory; and
    a processor coupled to the memory and controlling the display, the processor being configured to:
    switch from display of a first sectional image of the pair of mutually related sectional images to display of a combined sectional image generated from the first sectional image, in a case in which a change instruction is received to change from a slice position of the pair of mutually related sectional images being displayed at the display to a sectional image at a different slice position.

2. The image display device of claim 1, wherein the change instruction is a successive change instruction, which is an instruction to successively change a slice position of a sectional image.

3. The image display device of claim 2, wherein, in a case in which the successive change instruction is received, the processor is further configured to display a sectional image of a slice position of the pair of mutually related sectional images indicated by the successive change instruction, and a combined sectional image that corresponds to the slice position of the pair of mutually related sectional images indicated by the successive change instruction.

4. The image display device of claim 2, wherein, in a case in which the successive change instruction is received, the processor is further configured to:
    generate the combined sectional image corresponding to a slice position of the first sectional image from a second sectional image of the pair of mutually related sectional images; and
    successively perform switching from the second sectional image that is being displayed to the combined sectional image.

5. The image display device of claim 4, wherein the processor is configured to generate the combined sectional image by combining two frames of the second sectional image that are close to a slice position corresponding to the combined sectional image at a combination proportion according to a slice position corresponding to the combined sectional image and to slice positions corresponding to the two frames of the second sectional image.

6. The image display device of claim 4, wherein, in a case in which the successive change instruction is received, the processor is further configured to:
    generate a combined sectional image corresponding to the slice position of the first sectional image from the second sectional image of the pair of mutually related sectional images;
    switch the display of the first sectional image from the first sectional image being displayed to the first sectional image that corresponds to the slice position indicated in the successive change instruction; and
    in conjunction with the switching, successively switch the display of the second sectional image from the second sectional image being displayed to the combined sectional image.

7. The image display device of claim 4, wherein the processor is further configured to switch the display of the second sectional image from the combined sectional image being displayed to the second sectional image corresponding to a slice position that is closest to a slice position corresponding to the combined sectional image, after receiving the successive change instruction.

8. The image display device of claim 4, wherein the processor is further configured to:
    in a case in which the slice position indicated in the successive change instruction is a slice position having a largest value in the first sectional image, employ the second sectional image corresponding to the largest value for display of the second sectional image; and
    in a case in which the slice position indicated in the successive change instruction is a slice position having a smallest value in the first sectional image, employ the second sectional image corresponding to the smallest value for display of the second sectional image.

9. The image display device of claim 4, wherein the processor is configured to generate a combined sectional image corresponding to a slice position between a predetermined plurality of slice positions corresponding to the first sectional image.

10. The image display device of claim 4, wherein the processor is further configured to:
    after a successive change instruction has been received for a slice position from a first slice position to a second slice position, and in a case in which a further successive change instruction is received for a third slice position during a period in which successive switching of the combined sectional image is being performed according to the successive change instruction,
    stop successively performing switching from the second sectional image that is being displayed to the combined sectional image and, after displaying the second sectional image at a slice position close to the second slice position in a successive switching direction, successively switch from the sectional image being displayed to the combined sectional image corresponding to the third slice position.

11. The image display device of claim 4, wherein the processor is further configured to:

after a successive change instruction has been received for a slice position from a first slice position to a second slice position, and in a case in which a further successive change instruction is received for a third slice position during a period in which successive switching of the combined sectional image is being performed according to the successive change instruction, generate, for display of the second sectional image, a new combined sectional image combined from the combined sectional image being displayed and the second sectional image, at a combination proportion according to a slice position corresponding to the combined sectional image being displayed and to the third slice position, and stop successively performing switching from the second sectional image that is being displayed to the combined sectional image and successively switch to the new combined sectional image.

* * * * *